United States Patent
Dougherty et al.

(10) Patent No.: US 9,999,496 B2
(45) Date of Patent: *Jun. 19, 2018

(54) MULTIPLE IMPLANT CONSTRUCTIONS AND FIXATION METHODS ASSOCIATED THEREWITH

(71) Applicant: Tenjin LLC, Brazoria, TX (US)

(72) Inventors: Christopher P. Dougherty, Rogers, AR (US); Gary R. Heisler, Brazoria, TX (US); Robert A. Van Wyk, St. Pete Beach, FL (US)

(73) Assignee: TENJIN LLC, Brazoria, TX (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/662,664

(22) Filed: Jul. 28, 2017

(65) Prior Publication Data

US 2017/0319327 A1    Nov. 9, 2017

Related U.S. Application Data

(63) Continuation of application No. 15/256,945, filed on Sep. 6, 2016, now Pat. No. 9,717,587, which is a
(Continued)

(51) Int. Cl.
*A61F 2/08* (2006.01)
*A61B 17/04* (2006.01)
(Continued)

(52) U.S. Cl.
CPC ........ *A61F 2/0811* (2013.01); *A61B 17/0401* (2013.01); *A61B 17/0483* (2013.01);
(Continued)

(58) Field of Classification Search
CPC .......... A61F 2/0811; A61F 2002/0858; A61B 17/0401; A61B 2017/044; A61B 2017/0409; A61B 2017/0445
See application file for complete search history.

(56) References Cited

U.S. PATENT DOCUMENTS

| | | |
|---|---|---|
| 5,100,417 A | 3/1992 | Cerier |
| 5,152,765 A | 10/1992 | Ross |

(Continued)

OTHER PUBLICATIONS

"Value Analysis Brief—Healix Advance™ Knotless Anchor", DePuy Synthes Mitek Sports Medicine, a division of DePuy International Limited, a Johnson & Johnson company, pp. 1-5, 2013.

(Continued)

*Primary Examiner* — Julian W Woo
(74) *Attorney, Agent, or Firm* — Chalin A. Smith; Smith Patent, LLC

(57) ABSTRACT

Using the simplified placement system and method for a tissue graft anchor of the present invention, a surgeon may introduce one or more sutures into a hole in a boney tissue, apply a precise amount of tension to the sutures to advance a soft tissue graft to a desired location, and then advance the anchor into the bone, preferably while maintaining the requisite pre-determined suture tension and without introducing spin to the suture. Particularly preferred embodiments of the present invention relate to multi-anchor constructs. Multi-anchor constructs of the present invention may employ threaded implants exclusively, push-in implants exclusively, or a combination of threaded and push-in implants.

15 Claims, 33 Drawing Sheets

Related U.S. Application Data continuation-in-part of application No. 15/012,060, filed on Feb. 1, 2016, now Pat. No. 9,566,060, which is a continuation-in-part of application No. 14/972,662, filed on Dec. 17, 2015, now Pat. No. 9,795,374, which is a continuation of application No. 14/636,389, filed on Mar. 3, 2015, now Pat. No. 9,226,817.

(60) Provisional application No. 61/966,744, filed on Mar. 3, 2014, provisional application No. 61/998,391, filed on Jun. 26, 2014, provisional application No. 61/998,766, filed on Jul. 7, 2014, provisional application No. 61/999,405, filed on Jul. 26, 2014, provisional application No. 62/284,151, filed on Sep. 21, 2015, provisional application No. 62/389,039, filed on Feb. 16, 2016.

(51) Int. Cl.
*A61B 17/00* (2006.01)
*A61B 17/06* (2006.01)
*A61B 90/00* (2016.01)

(52) U.S. Cl.
CPC *A61B 17/0485* (2013.01); *A61B 2017/00477* (2013.01); *A61B 2017/044* (2013.01); *A61B 2017/0409* (2013.01); *A61B 2017/0427* (2013.01); *A61B 2017/0445* (2013.01); *A61B 2017/0458* (2013.01); *A61B 2017/0496* (2013.01); *A61B 2017/06042* (2013.01); *A61B 2090/034* (2016.02); *A61B 2090/064* (2016.02); *A61F 2002/0841* (2013.01); *A61F 2002/0858* (2013.01); *A61F 2002/0888* (2013.01)

(56) References Cited

U.S. PATENT DOCUMENTS

| | | | |
|---|---|---|---|
| 5,217,486 A | 6/1993 | Rice | |
| 5,584,860 A | 12/1996 | Goble | |
| 5,827,291 A | 10/1998 | Fucci | |
| 5,948,000 A | 9/1999 | Larsen | |
| 5,957,953 A | 9/1999 | DiPoto | |
| 6,416,324 B1 | 7/2002 | Day | |
| 6,544,281 B2 | 4/2003 | El Attrache et al. | |
| 6,641,597 B2 | 11/2003 | Burkhart | |
| 6,712,838 B2 | 3/2004 | D'Aversa et al. | |
| 7,063,702 B2 | 6/2006 | Michelson | |
| 7,322,978 B2 | 1/2008 | West | |
| 7,329,264 B2 | 2/2008 | Merves | |
| 7,329,271 B2 | 2/2008 | Koyfman et al. | |
| 7,357,810 B2 | 4/2008 | Koyfman et al. | |
| 7,585,311 B2 * | 9/2009 | Green | A61B 17/0401 606/232 |
| 8,100,942 B1 | 1/2012 | Green et al. | |
| 8,202,295 B2 | 6/2012 | Kaplan | |
| 8,435,264 B2 | 5/2013 | Sojka | |
| 8,465,522 B2 | 6/2013 | Burkhart | |
| 8,690,915 B2 | 4/2014 | Hootstein | |
| 8,709,040 B2 | 4/2014 | Anderhub | |
| 8,758,367 B2 | 6/2014 | Phillipon | |
| 8,814,905 B2 | 8/2014 | Sengun | |
| 8,858,596 B2 | 10/2014 | Robiso | |
| 9,095,331 B2 | 8/2015 | Hernandez | |
| 9,226,817 B2 | 1/2016 | Dougherty | |
| 9,370,351 B2 | 6/2016 | Sojka | |
| 9,386,976 B2 | 7/2016 | Mayer | |
| 9,649,104 B2 | 5/2017 | Lunn | |
| 9,717,587 B2 * | 8/2017 | Dougherty | A61F 2/0811 |
| 2006/0100627 A1 | 5/2006 | Stone et al. | |
| 2009/0306671 A1 | 12/2009 | Mccormack et al. | |
| 2009/0312794 A1 | 12/2009 | Nason | |
| 2009/0312795 A1 | 12/2009 | Barbieri | |
| 2014/0277128 A1 | 9/2014 | Moore et al. | |
| 2016/0367357 A1 | 12/2016 | Dougherty et al. | |
| 2017/0000476 A1 | 1/2017 | Dougherty et al. | |

OTHER PUBLICATIONS

"Healix Advance™ Knotless Anchor for rotator cuff repair", DePuy Mitek Inc., Johnson & Johnson Medical Limited, pp. 1-4, 2015.

"Healix Knotless™ Suture Anchor", DePuy Mitek, pp. 1-7, Feb. 2012.

Product Brochure for "SpeedBridge™ and SpeedFix™ Knotless Rotator Cuff Repair using the SwiveLock® and FiberTape® Surgical Technique", Arthrex, Inc., 2013.

Product Brochure for "Healix Knotless™ Anchor", DePuy Mitek, Inc., 2012.

"Optimized Sports Medicine Solutions", Parcus Medical, LLC, 2013.

"ReelX STT™ Knotless Anchor System", Stryker® Corporation, 2010.

"PopLok 3.5 & 4.5 MM", ConMed Corporation, 2015.

* cited by examiner

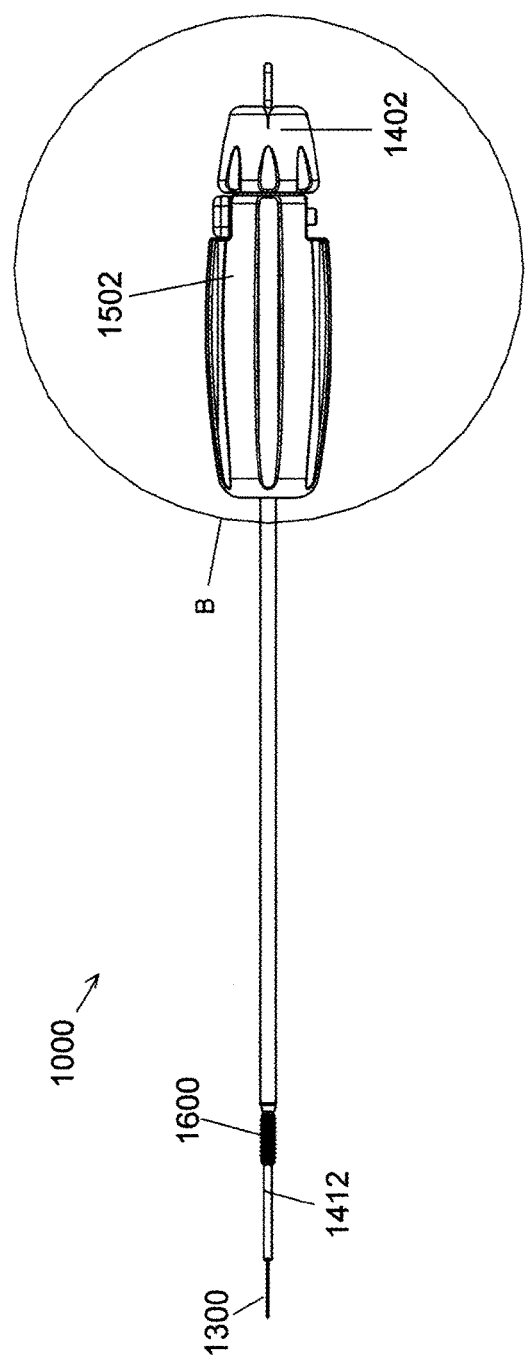
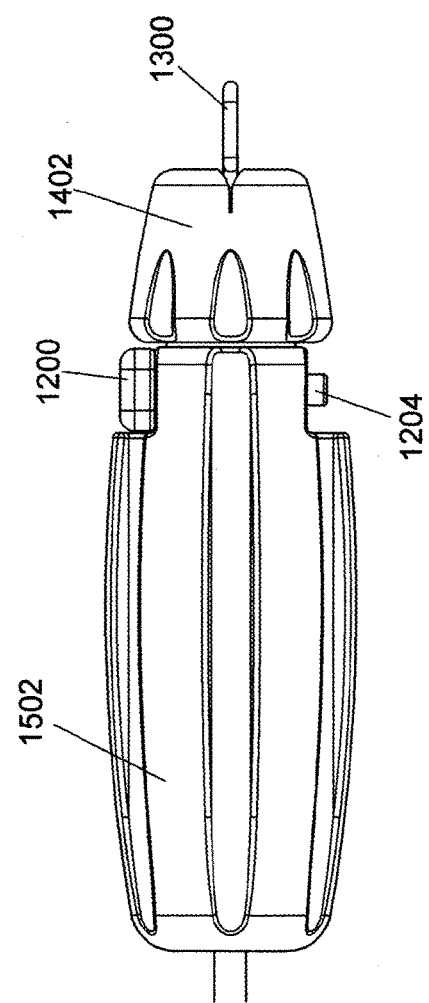
Fig. 5
Fig. 6

MULTIPLE IMPLANT CONSTRUCTIONS AND FIXATION METHODS ASSOCIATED THEREWITH

PRIORITY

This application is a continuation of U.S. patent application Ser. No. 15/256,945, filed Sep. 6, 2016 (now U.S. Pat. No. 9,717,587 issued Aug. 1, 2017), which, in turn is a continuation-in-part of U.S. patent application Ser. No. 15/012,060 filed Feb. 1, 2016 (now U.S. Pat. No. 9,566,060 issued Feb. 14, 2017), which, in turn, is a continuation-in-part of U.S. patent application Ser. No. 14/972,662 filed Dec. 17, 2015, which, in turn, is a continuation of U.S. patent application Ser. No. 14/636,389 filed Mar. 3, 2015 (now U.S. Pat. No. 9,226,817 issued Jan. 5, 2016), which, in turn, claims the benefit of U.S. Provisional Application Ser. No. 61/966,744 filed Mar. 3, 2014; 61/998,391 filed Jun. 26, 2014; 61/998,766 filed Jul. 7, 2014; and 61/999,405 filed Jul. 26, 2014, the contents of each of which are hereby incorporated by reference in their entirety. This application also claims the benefit of U.S. Provisional Application Ser. No. 62/284,151 filed Sep. 21, 2015 and 62/389,039 filed Feb. 16, 2016. The contents of the afore-noted priority applications are hereby incorporated by reference in their entirety.

TECHNICAL FIELD OF THE INVENTION

The present invention relates generally to the field of endoscopic and arthroscopic surgery and suture anchor systems for use therein. More particularly, the invention relates to knotless suture anchor systems and methods utilized to secure a soft tissue to boney surface through the placement of a matrix of implants. Specifically, the invention relates to simplified methods by which the surgeon may produce multi-implant constructs for the purpose of compressing a portion of a tissue graft to a boney surface for the purpose of reattachment thereto through healing.

BACKGROUND OF THE INVENTION

The use of implants to affix tissue grafts to bone is well known in the orthopedic arts. Common procedures in which such implants are used include, for example, the repair of rotator cuff tears, and the repair of torn ligaments in the knee, among others. In these procedures, a socket is drilled or punched in the bone at the attachment site and a graft is secured to the bone using an implant placed in the socket. The graft may be secured to the implant by sutures, or, alternatively, an end of the graft may be placed in the socket and secured directly by an implant.

In rotator cuff repair implants commonly referred to as "anchors" are used. These anchors occur in two types: conventional anchors in which the suture is passed through the cuff after anchor placement, and "knotless" anchors in which the suture is passed through the cuff prior to anchor placement. In the former case, the graft is secured in place by tying knots in the suture after it has been passed through the cuff so as to secure the cuff in the desired location. Conversely, as the name implies, when using a knotless anchor the sutures are passed through the cuff and through a feature of the anchor such that when the anchor is inserted into the socket, the suture position is secured by the anchor. The tying of knots is not required. This is particularly advantageous when performing endoscopic (arthroscopic) repairs since the tying of knots arthroscopically through a small diameter cannula may be difficult for some surgeons and, moreover, there is an opportunity for tangling of the sutures.

Many anchors, both conventional and knotless, are supplied to the surgeon mounted on a driver—a device that the surgeon uses to place the anchor in the prepared socket in the bone. In the case of threaded anchors, the driver has a form like that of a screwdriver, and indeed functions in the same manner. The proximal portion of the device forms a handle that is grasped by the surgeon. Distal to the handle, an elongate distal portion has formed at its distal end features for transmitting torque to an implant. Some anchors, generally metallic anchors such as, for instance, the Revo® Suture Anchor by Conmed Corporation (Utica, N.Y.) and Ti-Screw Suture Anchor by Biomet Corporation (Warsaw, Ind.), have a protruding (male) proximal portion with a cross-section suitable for transmitting torque (typically hexagonal or square) and a transverse eyelet formed therein. The driver for such devices has a complimentary socket (female) formed in its distal end and a cannulation that extends from the interior of the socket to the proximal handle portion of the device. Sutures loaded into the eyelet of the anchor extend through the driver cannulation (or "lumen") and are removably secured to the handle so as to retain the anchor in the socket of the driver. Such anchors are referred to in the orthopedic arts as "pre-loaded", meaning that sutures come loaded into an anchor that is ready for placement by the surgeon using the associated driver.

Other threaded anchors have a socket (female) formed in their proximal ends. Once again, the socket has a cross-section suitable for transmitting torque that is typically polygonal, usually square or hexagonal. Typical of these are the V-LoX™ family of titanium suture anchors by Parcus Medical (Sarasota, Fla.) and the ALLthread™ anchors by Biomet Corporation (Warsaw, Ind.). The drivers for such devices have a protruding (male) torque-transmitting feature complementary to the socket (female) formed in the proximal end of the anchor. These drivers may be cannulated to accommodate sutures that are preloaded into the anchor in the manner previously described, with the sutures being either for the purpose of securing tissue after anchor placement, or for the purpose of removably securing the anchor to the driver, wherein the sutures are released from the driver after the anchor is placed in the bone and subsequently removed and discarded so as to allow removal of the driver from the anchor. The depth of the socket in the proximal end of the implant must be sufficient to enable transmission of the requisite torque needed for anchor placement without deforming or fracturing the implant. As the maximum depth of the torque-transmitting portion is generally limited only by the configuration of the anchor, it is considered to be matter of design choice. Indeed, the implant may have a cannulation that extends axially through the implant as well as a torque-transmitting cross-section forming a substantial proximal portion or the entirety of the implant's length. Implants of the Bio-Tenodesis Screw™ System by Arthrex, Inc have a cannulation with a constant torque-transmitting cross-section, and are used with a driver having a torque-transmitting portion that extends beyond the distal end of the anchor, wherein the portion of the driver extending beyond the anchor and a suture loop in the driver cannulation are used together to insert the end of a graft into a prepared socket prior to placement of the implant.

Knotless suture anchor fixation is a common way of repairing soft tissue that has been torn from bone. Illustrative examples of such "knotless" anchors include the Allthread™ Knotless Anchors by Biomet Incorporated (Warsaw, Ind.), the SwiveLock® Knotless Anchor system by Arthrex, Incorporated (Naples, Fla.), the HEALIX Knotless™ Anchors by Depuy/Mitek, Incorporated (Raynham, Mass.) and the Knotless Push-In Anchors such as the Knotless PEEK CF Anchor by Parcus Medical (Sarasota, Fla.). The procedure requires drilling or punching of holes into a properly prepared boney surface. After suture has been passed through soft tissue the suture anchor is introduced into the socket and driven into the socket using a mallet or by screwing the anchor into the socket using a driver device. These driver devices typically resemble a screwdriver in form, having a proximal handle portion for applying torque or percussive force, and an elongate rigid distal portion having at its distal end a torque or percussive force-transmitting configuration. In the case of torque-transmitting drivers used with threaded anchors, the distal end of the driver typically has an elongate hexagonal or square distally extending portion that, through coupling with a lumen in the anchor having a complementary cross-section, transmits torque to the anchor. The lumen may extend through anchor so that the distal portion of the driver protrudes from the distal end of the anchor and rotates with the anchor during anchor placement.

Because the suture is drawn into the prepared socket along with the anchor during anchor placement, it is essential that a suitable length of suture extends between the graft and the anchor so that when the anchor is suitably positioned within the socket, the graft is properly positioned. Determining the proper length of suture to allow between the anchor and the graft so as to achieve optimal graft positioning is complicated since suture may twist (a process referred to in the orthopedic arts as "suture spin") during anchor placement, thereby shortening the effective length and changing the final graft position and/or undesirably increasing the suture tension.

U.S. Pat. No. 6,544,281 to ElAttrache et al. describes a cannulated anchor placement system having a rotating inner member (which acts as the anchor driver) and a stationary outer member, wherein the rotating inner member serves to drive the threaded anchor. The rotating "driver" extends past the distal end of the anchor and is inserted into a prepared socket in the boney surface. A suture loop formed distal to the distal end of the driver "captures" or "secures" sutures attached to a graft or the graft itself to the distal end of the driver. The distal end of the driver is then inserted into the socket to a proper depth for anchor placement thereby drawing the graft to the desired position prior to placement of the anchor. The anchor is then threaded into the socket to the predetermined depth. This system constitutes an improvement over other commercially available alternatives. However, because the graft or sutures are secured to or pass through the distal end of the rotating inner (or "driver"), torque is transmitted not only to the anchor but also to the graft or sutures attached thereto by the suture loop. Accordingly, twisting of the sutures or graft frequently occurs, thereby changing the resulting suture tension and/or the graft position (a process referred to in the orthopedic arts as "graft shift").

U.S. Pat. No. 8,663,279 by Burkhart et al. describes a knotless anchor system similar in construction to that of ElAttrache et al. A "swivel" implant having formed therein an eyelet is releasably and pivotably mounted to the distal end of a driver distal portion that extends distally beyond the distal end of an anchor. After sutures are passed through the graft, they are threaded into the eyelet of the swivel implant at the distal end of the driver. The distal end of the driver with the swivel implant is then inserted into the socket. By pulling on the suture tails, the graft is moved into position and secured by screwing the anchor into the socket. However, because the sutures/graft are secured to the driver by means of the swivel eyelet implant, the torque that may be transmitted to the sutures/graft is limited. Torque transmission is not eliminated since the swivel implant is retained in the driver distal end by a suture loop under tension, which extends through the cannula of the driver to the driver's proximal end where the suture ends are cleated. While an improvement over the ElAttrache anchor system, suture spin is not eliminated in all cases, and indeed, cannot be since the suture-retaining implant is mounted to the driver, which rotates during anchor placement. As such, some level of torque transmission due to friction between the driver distal end and the swivel eyelet implant is inevitable.

Other knotless anchors such as the ReelX STT™ Knotless Anchor System by Stryker® Corporation (Kalamazoo, Mich.) and PopLok® Knotless Anchors by ConMed Corporation (Utica, N.Y.) have complex constructions and require that the surgeon perform a sequence of steps to achieve a successful anchor placement with the desired suture tension and proper cuff position. The sequence of steps adds to procedure time and creates opportunities for failure of the placement procedure if a step is not performed properly.

Accordingly, there is a need in the orthopedic arts for a knotless anchor system that allows the surgeon to establish the graft position, and, while maintaining that position, place the anchor without changing the suture tension or causing a shift in the graft position due to suture spin. Furthermore, if the anchor is threaded, placement of the anchor in the socket must occur without spinning of the suture.

Fixation methods previously herein described, as well as in parent application Ser. No. 15/012,060 filed Feb. 1, 2016 and Ser. No. 14/972,662 filed Dec. 17, 2015 cited above and incorporated by reference herein, are used in what is generally referred to as "single row" repair of rotator cuff tears. Specifically, suture(s) placed through the cuff is/are secured to a single anchor lateral to the lateral margin of the cuff, the anchors forming a single row lateral to the cuff's edge. However, these single-row repair methods can achieve only partial restoration of the original footprint of the tendons of the rotator cuff. Accordingly, "double row" repairs of rotator cuff tears are increasing in popularity. In such double row techniques, one or more sutures loaded to a first implant medial to the edge of the cuff is/are passed over the cuff and affixed to a second implant, which is placed lateral to the edge of the cuff, the suture between the anchors being tensioned so as to apply a compressive force to the tissue therebeneath. These double-row (DR) repair methods present many biomechanical advantages and exhibit higher rates of tendon-to-bone healing.

In U.S. Pat. Nos. 7,585,311 and 8,100,942, Green et al. describe double row techniques for rotator cuff repair. In particular, Green et al. teach a method in which a first anchor with sutures affixed thereto is placed medial to the edge of the rotator cuff. Thereafter, a second anchor is placed lateral to the edge of the cuff. Suture from the first anchor is then passed over the cuff, tensioned, and then affixed to the second anchor. The second anchor is irremovably placed prior to tensioning of the suture and fixation thereto.

When fixation of the suture in the anchor is complete, the tension in the suture between the anchors is established, the suture being irremovably affixed to the second anchor. If the tension is judged by the surgeon to be unacceptable (i.e., either inadequate or too great), or if the placement location is unacceptable, it becomes necessary to prepare a socket in an alternate location and repeat the steps previously described since the suture is permanently affixed to the originally placed second anchor and the anchor is not readily removable from the socket. Critically, currently available implant systems cannot be repositioned using the original anchor, nor can they be removed and replaced without compromising the eyelet/anchor construct.

SUMMARY OF THE INVENTION

A primary objective of the present invention is to provide improved means and methods of attaching soft tissues (i.e., "grafts") to bone in situ. The embodiments of the instant invention are described hereinbelow as a system and method for producing a matrix of implants for the anchoring of a graft to bone. Any graft fixation system which uses an implant placement system with an optionally cannulated non-rotating tensioning device (i.e., the relatively fixed "inner assembly") positioned within a lumen of a cannulated driver (i.e., the relatively movable "outer assembly") to tension sutures in a prepared socket for the placement of a simple one-piece cannulated anchor are contemplated by the present invention. Illustrative aspects and embodiments of the present invention in accordance with the foregoing objective are as follows: In a first aspect, the present invention provides prosthetic implants and systems for their placement in a target boney surface for the knotless securing of a soft tissue graft thereto. The instant invention contemplates a novel placement system including a non-rotating cannulated tensioning device ("inner assembly") positioned within a rotationally and axially movable cannulated driver ("outer assembly"). In a preferred embodiment, a distal element of the tensioning device extends distally beyond the distal end of the cannulated driver. A cannulated threaded implant (or "anchor") is removably mounted to the torque-transmitting distal portion of the driver. Sutures placed in the graft are drawn into the distal end of the elongate distal portion of the cannulated tensioning device, which extends beyond the distal end of the implant. If a threaded implant is used, the distal end of the cannulated driver preferably includes torque-transmitting features that, together with complementary features formed in the proximal portion of the implant or anchor, allow the transmission of torque thereto. If an interference plug-type anchor is used, the distal end of the driver is preferably configured to transmit axial force to the anchor, the distal end of which has suitable complementary features to enable secure attachment.

In operation, sutures placed in the graft are drawn into the distal end of the tensioning device. The elongate distal portion of tensioning device is inserted into a properly prepared socket in the target boney surface so that the distal end of the tensioning device, with its sutures is positioned at the bottom of the socket. Tension is then applied to the sutures by pulling on their proximal ends, which extend beyond the proximal portion of the tensioning device to move the graft into the desired position, namely into the prepared socket adjacent to the distal element of the tensioning device. The desired tension may be maintained by cleating proximal portions of the suture(s) into slots optionally formed in the handle of the tensioning device. The anchor (or interference screw) may then be screwed, threaded or otherwise driven into the socket, thereby trapping the sutures or graft between the anchor exterior surface and the socket wall. Critically, twisting of the sutures or graft is prevented by the non-rotating distal portion of the tensioning device that remains distal to the anchor distal end during anchor placement. In addition, tension on the sutures and the position of the graft are maintained during placement of the anchor throughout the procedure. After anchor placement, the driver and tensioning device are withdrawn, removed from the site, at which point the sutures may be trimmed to complete the procedure.

In contrast to the Burkhart and ElAttrache anchor systems, suture tensioning and establishment of the graft position are not accomplished using the driver's distal end or using an implant positioned in the driver's distal end. Rather, suture tension and graft position are established and maintained by the distal portion of a non-rotating tensioning device that extends beyond the driver and anchor distal ends. Because of this, the transmission of torque to the sutures and/or graft by the driver present in the Burkhart and ElAttrache systems is eliminated along with its associated suture or graft spin.

The system and method of the instant invention provide a simplification over other currently available anchoring methods and hardware in that fewer steps are required and moreover the anchor has a simple, single-piece construction. The anchor system is scalable and, due to its simple construction, may be used with anchors smaller than those permitted using other currently available systems. The composition and construction in the anchor may be readily modified simply by changing the material from which it is constructed, by increasing or reducing the diameter or length of the anchor, by increasing or decreasing the wall thickness of the anchor, by modifying the profile of the exterior, or by any combination of these means. All such modifications are contemplated as within the scope of the present invention.

In another aspect, the present invention provides a method for affixing a soft tissue graft to a target boney surface, the method comprising the steps of:
  a. providing a placement system having an optionally cannulated non-rotating tensioning device ("inner assembly") and a cannulated driver device ("outer assembly"), wherein the tensioning device is positioned within the cannulation or "lumen" of the driver device,
  b. positioning a cannulated anchor onto the distal torque-transmitting portion of the driver, over a distally extending element of the tensioning device,
  c. producing a suitably configured hole (i.e., "socket") in a prepared boney surface at a desired target location using a drill, tap, punch or equivalent hole-producing device,
  d. drawing sutures from the graft into the lumen of the tensioning device,
  e. inserting the distal end of the tensioning device into the socket,
  f. applying tension to the sutures to draw the graft to a desired position,
  g. placing the anchor (or interference screw) in the socket,
  h. withdrawing the placement system,
  i. trimming the suture tails, and
  j. optionally repeating steps (c) through (i) as required.

In an alternate embodiment of the present invention, identical in all aspects to the previous embodiment except as subsequently described, the tubular distal portion of the tensioning device is replaced by a rod having formed at its distal end a sharpened fork portion. Two (or more) parallel, axially extending tines form the fork, the tines being spaced apart so that sutures may slide freely through the channel(s) formed between the tines. An anchor placement system commensurate with such an embodiment is used in the following manner: First, a cannulated threaded implant is removably mounted to the torque-transmitting distal portion of the driver. Sutures placed in the graft are then positioned in the channel(s) of the distal fork portion of the tensioning device. The elongate distal portion of the tensioning device with the sutures positioned within its distal channel is then inserted into a prepared socket so that the distal end of the tensioning device with its sutures is positioned at the bottom of the socket. Tension is then applied to the sutures by pulling on their proximal ends to draw the graft into the desired position. The desired tension and graft position may be maintained by cleating the suture proximal portions in slots optionally formed in the handle of the tensioning device. The anchor is then screwed, threaded or otherwise driven into the socket by the driver, thereby trapping the sutures or graft between the anchor exterior surface and the socket wall. Twisting of the sutures or graft is prevented by the non-rotating distal fork portion of the tensioning device, which remains distal to the anchor distal end during anchor placement. The tension on the sutures and the position of the graft are maintained during placement of the anchor. After anchor placement, the driver and tensioning device are removed from the site and the sutures trimmed to complete the procedure.

A further aspect of the instant invention addresses the placement of small diameter implants. In particular, the placement of small diameter implants using a cannulated tensioning device such as presently described may be problematic since the cannulation in the implant decreases with the implant diameter. This decrease in the implant cannulation diameter necessitates a corresponding decrease in the cannulation diameter of the tensioning device distal portion. As a result, the diameter of the cannulation in the tensioning device distal portion may potentially be insufficient to accommodate the number and size of sutures required for the proper securing of an associated graft. Accordingly, in yet another embodiment of the present invention for use predominantly with small diameter implants, an elongate element formed from a suitable metallic or polymeric material forms a retention loop distal to the distal end of the distal portion of the cannulated tensioning device, with the proximal ends of the elongate element extending to the proximal end of the tensioning device where they are removably secured. One or more sutures are loaded into the distal retention loop formed by the elongate element. Thereafter, tensioning of the sutures and placement of the implant are as previously herein described, for example following the steps utilized in connection with the previously described tensioning device including a "forked" distal end. After the implant is properly placed, the proximal ends of the elongate element are freed and the elongate element is removed from the site by withdrawing of the proximal ends. In a preferred embodiment, the elongate element is formed of a nitinol wire.

Yet another aspect of the instant invention addresses the construction of small diameter implants. The minimum size of threaded metal anchors that may be created and their configurations are limited by the ability of a machine tool to produce them. The configurations of small metal anchors used in, for instance, hand surgery are limited to those that require the tying of knots after passing suture through a graft. Similarly, threaded anchors made of polymeric materials such as PEEK are limited in their minimum size by the strength of the underlying material. When these threaded anchors become very small, the ability of a driver to transmit torque to the implant is limited by the resistance to deformation of the torque-transmitting features of the implant. When conventional (i.e., not knotless) anchors are used, the graft must be secured in position by tying knots on the surface of the graft opposite the attachment site. These knots are frequently perceptible beneath the skin of the patient and can create irritation for the patient. Accordingly, there is a need for very small knotless anchors configured for small joint repairs.

In the course of the present invention, it was discovered that anchor systems of the present invention that use an elongate wire element as described above may be miniaturized through the use of advanced materials having high tensile strengths along with the use of advanced manufacturing techniques. Specifically, very small knotless anchors may be produced from ceramic materials using a process known as "Ceramic Injection Molding" or simply "CIM". The tensile strength of PEEK material is typically between 10,000 and 15,000 psi. In comparison, the tensile strength of alumina is generally in excess of 200,000 psi. Furthermore, recently developed materials such as Zirconia Toughened Alumina (ZTA) by Coorstek Inc. (Golden, Colo.) have a high degree of toughness in addition to high tensile strength. These materials, being ceramic, do not have a yield point and therefore do not deform under load. The high tensile strength and the absence of yielding under load of an implant constructed of such ceramic materials allow torque to be transmitted to the implant through features that are not producible by the machining of metal or that would fail in use if formed from a polymeric material such as PEEK. Thus, ceramic knotless anchors of the present invention may be produced in sizes and configurations not possible using prior art technology.

Accordingly, in certain embodiments of the present invention, the distal torque-transmitting portion of the driver may also be ceramic, formed by ceramic injection molding so as to allow miniaturization of the torque-transmitting features. In other embodiments, the torque-transmitting portion of the implant is a laterally extending slot in the proximal end of the implant similar to a standard screwdriver slot, wherein the ceramic material from which the implant is formed is sufficient to ensure that the anchor does not fail by fracture proximal to its distal end or by failure of the torque-transmitting proximal slot. In yet other embodiments, the ceramic implant is an interference plug, wherein the high elastic modulus and high strength of the ceramic materials is beneficial for small and miniature interference type anchors that are driven axially into a prepared socket. The high modulus and high strength of the materials allows the thickness of the wall between the central lumen and the outer surface to be reduced compared to interference type anchors produced from polymeric materials without reducing the compressive force which retains the one or more sutures between the outer wall of the implant and the wall of the socket.

As an improvement over the prior art, threaded implants placed using the systems of the present invention may be readily removed after placement. If the initial tensioning of a suture affixed in a prepared socket using a threaded implant and system of the present invention is determined by the surgeon to be suboptimal, the implant may be backed out of the socket using the same system used for its placement. The suture may then be re-tensioned and secured using the same implant that was removed. If. after placement and tensioning of a suture. the anchor position is found to be sub-optimal, the implant may be backed out of the socket in the same manner, after which a new socket may formed in an alternate location, and the suture may tensioned and retained in the new socket using the same implant removed from the original socket.

Another aspects of the anchor placement system of the present invention relates to the inclusion of a mechanism for releasably preventing relative axial and rotational movement between the driver and the tensioning device, such means optionally positioned within the cannulation (or "lumen") of the driver. In a first condition used during tensioning of the suture, relative axial and rotational motion of the driver relative to the tensioning device is prevented. In a second condition, used during placement of the anchor, the driver may be advanced axially on the tensioning device to bring the anchor to the socket, and rotated to screw the anchor into the socket, with the tensioning device remaining stationery so as to maintain suture tension and prevent twisting of the sutures.

In a particularly preferred embodiment, prevention of relative motion is provided by a removable key having one or more protrusions, coupled with features formed on the handles of the tensioning device and driver such that, when the features are in alignment, engagement by the one or more protrusions of the key prevents relative axial or rotational movement between the torque-transmitting driver and the tensioning device. Removal of the key allows the driver to be advanced distally and rotated relative to the tensioning device. Other embodiments are anticipated in which other means are used to releasably prevent relative motion.

In yet another aspect, like the previous in all other respects except as subsequently described, the suture attached to the graft is positioned within the distal fork and tensioned such that the proximal end of the graft is adjacent to the fork, the tension being maintained by cleating of the sutures on the tensioning device handle. The distal portion of the tensioning device with the graft is inserted into the prepared socket. The anchor is then threaded or driven into the socket as previously described, thereby trapping the graft proximal portion between the anchor exterior surface and a first portion of the socket wall, and the attached sutures between the anchor exterior surface and a second, laterally opposed portion of the socket wall. In a variation of the previous aspect, the graft may be pierced by the sharpened, distally extending members ("tines") of the distal fork. The distal portion of the tensioning element with the graft is inserted into the prepared socket. Once again, the anchor is then threaded or driven into the socket, thereby trapping the graft proximal portion between the anchor exterior surface and a portion of the socket wall.

In another variation of the previous aspect, the graft is pierced by the sharpened distally extending members of the distal fork a predetermined distance from the graft distal end such that when the distal portion of the tensioning element with the graft is inserted into the prepared socket, the proximal end of the graft protrudes above the opening of the socket. The anchor is then threaded or driven into the socket, thereby trapping the graft proximal portion between the anchor exterior surface and first and second laterally opposed portions of the socket wall.

In still yet another aspect, identical in form to the devices and insertion systems previously herein described, the tensioning device has a proximal handle portion that is an assembly of first and second rigid elements with an elastic element positioned therebetween. Applying a distal force to a first rigid element of the handle of the tensioning device causes deflection of the elastic element proportional to the tension in the graft attached to the distal fork. This allows the practitioner to measure the tension in the graft. By establishing the tension in the graft to a predetermined value prior to placement of the anchor, the tension may then be maintained at the predetermined value during anchor placement.

Another aspect of the present invention relates to the use of a family of knotless anchor placement systems in accordance with the present invention to allow tensioning of a suture prior to placement of an implant. The tension in the suture may be readjusted by removing the implant, adjusting the tension and resetting the implant in the same prepared socket. In a first embodiment, the system draws sutures into the central lumen of a non-rotating tensioning device located within the cannulation of a driver device, such that the tension on the sutures may established by pulling on the suture portions proximal to the insertion device handle. After satisfactory tension is achieved and maintained by cleating to the insertion device handle, an implant is threaded into the socket. The system is described in U.S. Pat. No. 9,226,817, the contents of which are hereby included by reference in their entirety.

A second system is like the first in that a non-rotating tensioning device is positioned within the cannulation of a driver device. However, unlike the first system, the tensioning device is not cannulated and the distal end of the tensioning device has formed thereon a "fork" such as described above, wherein sutures may be retained in the fork for tensioning prior to anchor placement. This system is described in U.S. Pat. No. 9,226,817, the contents of which are hereby included by reference in their entirety.

A third system is alike in form to the first system except that instead of drawing sutures into the central lumen of the non-rotating tensioning device, a suture retention loop is formed distal to the distal end of the insertion device by an elongate wire that extends to the proximal end of the insertion device. Sutures are loaded into this wire loop and maintained in position at the distal end of the insertion device thereby during tensioning of the sutures and anchor placement. Thereafter the elongate wire is removed. Details of the system are contained in a related co-pending application entitled "Ceramic Implant Placement Systems And Superelastic Suture Retention Loops For Use Therewith" Ser. No. 15/256,815 filed contemporaneously with the instant application, the contents of which are herein incorporated by reference in their entirety. The unique ability of these systems to establish tension in a suture prior to lateral anchor placement, and their ability to allow an implant to be removed and reinserted by the surgeon if modification of the tension is necessary, enable simplified methods for multi-anchor reattachment of soft tissue grafts to bone. Unlike prior art methods that utilize two-piece anchor systems (e.g., a suture retaining eyelet and a proximal interference screw or plug as in Burkhart, or an anchor and a suture securing "anchor top" as described by Green et al.), tensioning is accomplished prior to the placement of any implant. In addition, unlike prior art methods, the suture may be removably affixed by the lateral implant, with a lateral portion of the suture being trapped between at least a first portion of the implant outer surface and the wall of the socket in which it is placed. This stands in stark contrast to procedures and protocols outlined in the prior art, including the method of Green et al., wherein in the suture is fixedly secured to the second (lateral) anchor. Thus, the system and method of the present invention serves to reduce the number of steps that the surgeon must perform, thereby resulting in time and cost savings, and a reduction in the opportunity for error. To wit, if an error occurs, methods and devices of the present invention permit the easy removal of the single-piece implant for retensioning of the suture and reinsertion of the implant, or the relocation of the same implant if the original location is determined to be unsuitable.

Accordingly, in a preferred aspect, the present invention provides a method for affixing a soft tissue graft to a target boney surface, the method including the steps of:

a. affixing at least one suture to the bone medial to the lateral edge of the soft tissue by means of a first implant, such as cannulated knotless suture anchor, such that no portion of the implant lies lateral to the soft tissue edge;

b. passing a first length of suture from the first implant over the soft tissue;

c. forming a socket lateral to the edge of the soft tissue such that it is not underneath the soft tissue;

d. establishing a desired tension in the first length of suture; and e. placing the first implant in the socket so as to trap a portion of the first length of suture between at least a first portion of the implant and the wall of the socket so as to provide fixation.

In certain preferred embodiments, the lateral implant may be threaded so as to provide removable fixation to the suture. In such embodiments with removable fixation of the suture, the method of the present invention may also optionally include the following additional steps:

f. removing the lateral implant from the socket in which it was placed;

g. adjusting the tension in the first length of suture; and h. placing the same implant in the socket so as to trap a portion of the first length of suture between at least a first portion of the implant and the wall of the socket so as to provide removable fixation.

Alternatively, in another preferred embodiment, the following optional steps may be included:

f. removing the lateral implant from the socket in which it was placed;

g. forming a socket in a new location lateral to the edge of the soft tissue such that it is not underneath the soft tissue;

h. establishing a desired tension in the first length of suture; and i. placing the same implant in the socket so as to trap a portion of the first length of suture between at least a first portion of the implant and the wall of the socket so as to provide removable fixation.

Double row repairs of large rotator cuff tears may require constructs in which a matrix of medial and lateral implants are used. Sutures may span the tissue between a row of medial implants and a row of lateral implants so as to ensure reliable contact between the soft tissue and underlying bone in the region between the rows of implants. For example, an implant in the medial row may anchor multiple sutures that extend to multiple lateral implants as well as to adjacent medial row implants. In methods of the current invention, each tissue-spanning suture extending from a first medial anchor may be individually tensioned prior to being removably affixed to the bone by a second implant. If the tension in any suture of the construct is found to be unsuitable, the tension may be adjusted using methods previously herein described. Likewise, if the location of any anchor of a construct is found to be unsuitable, the implant may be relocated using methods previously herein described. Alternatively or additionally, if upon completion of forming a double row construct, the surgeon finds that a region of the rotator cuff is not securely compressed against the underlying bone (a condition referred to by surgeons as a "dog ear") one or more additional implants may be placed so as to span the region with tensioned sutures. Sutures from the supplemental implant(s) may be integrated into the previously formed construct by removing one or more implants of the construct, adding the spanning sutures from the supplemental implants, and tensioning and securing the sutures as previously herein described.

These and other aspects are accomplished in the invention herein described, directed to a system and method for producing a matrix of implants for the anchoring of a graft to bone. Further objects and features of the invention will become more fully apparent when the following detailed description is read in conjunction with the accompanying figures and examples. For example, because the implant systems and methods of the present invention provide removable fixation of the sutures to the underlying bone, numerous modifications may be made to the completed construct, or the construct may even be removed in its entirety. However, it is to be understood that both the foregoing summary of the invention and the following detailed description are of a preferred embodiment, and not restrictive of the invention or other alternate embodiments of the invention. In particular, while the invention is described herein with reference to a number of specific embodiments, it will be appreciated that the description is illustrative of the invention and is not constructed as limiting of the invention.

BRIEF DESCRIPTION OF THE FIGURES

Various aspects and applications of the present invention will become apparent to the skilled artisan upon consideration of the brief description of figures and the detailed description of the present invention and its preferred embodiments that follows:

FIG. 5 is a side elevational view of the objects of FIG. 2.

FIG. 6 is an expanded view of the objects of FIG. 5 at location B.

DETAILED DESCRIPTION OF THE PREFERRED EMBODIMENTS

Figure 1:
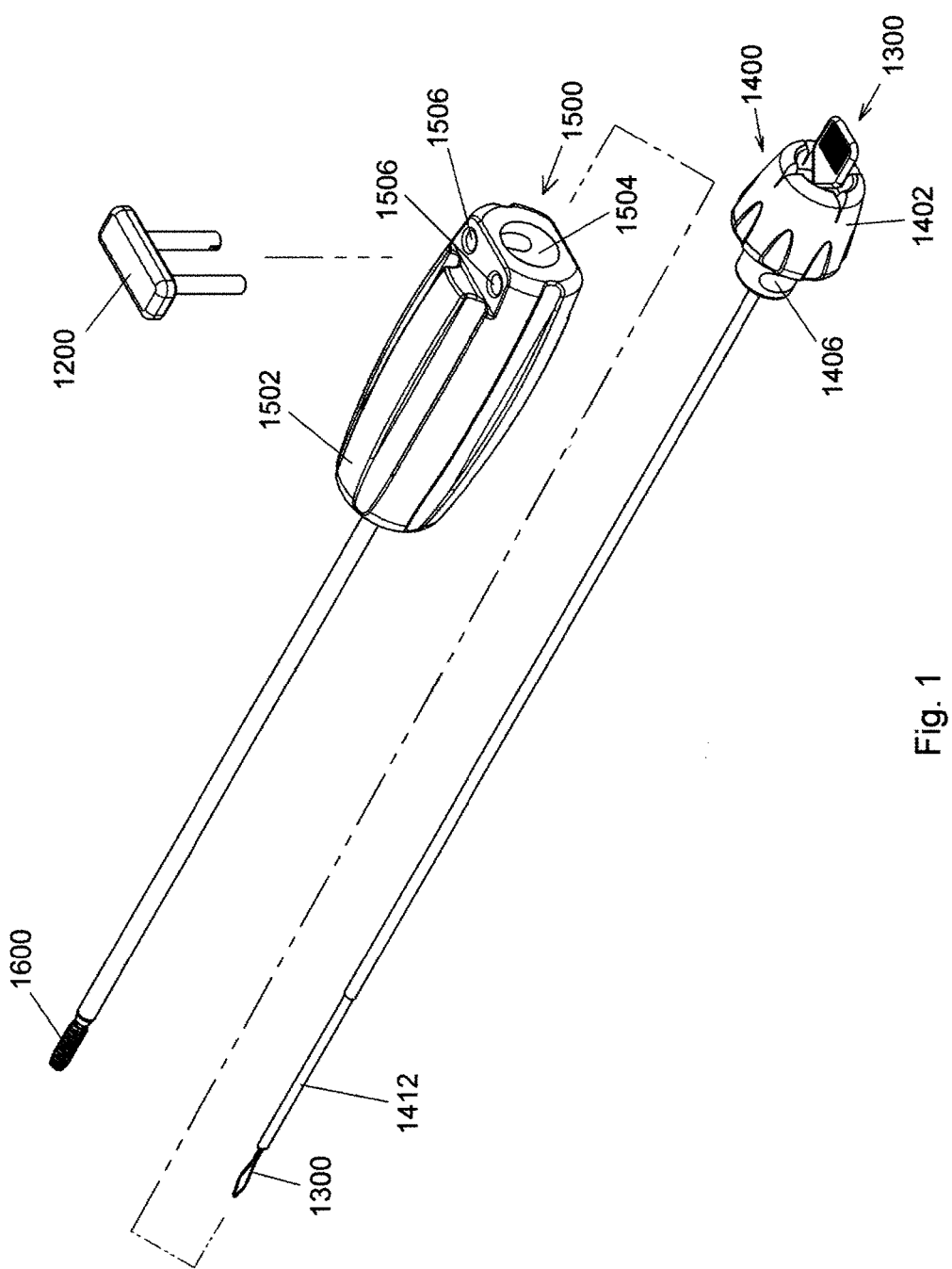
FIG. 1 is a perspective view of an exploded assembly of a first anchor placement system of the present invention.
Figure 2:
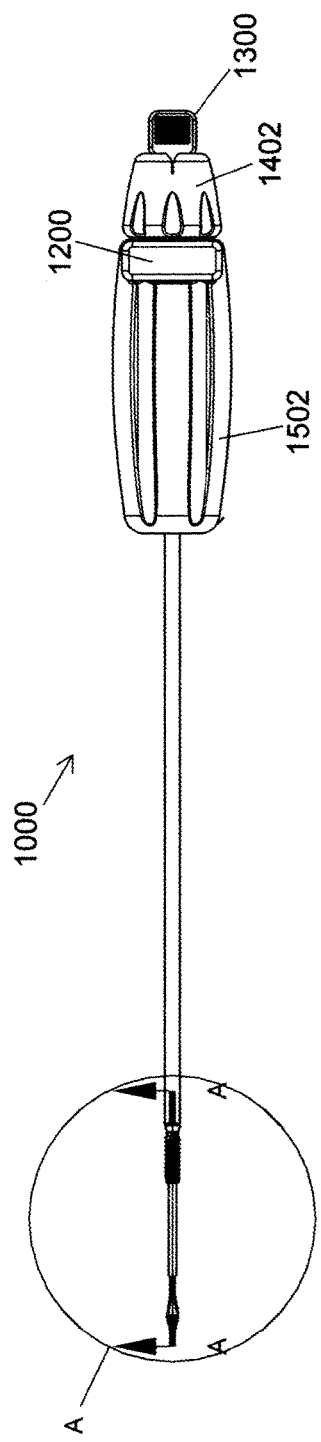
FIG. 2 is a plan view of the assembled system of FIG. 1.
Figure 3:
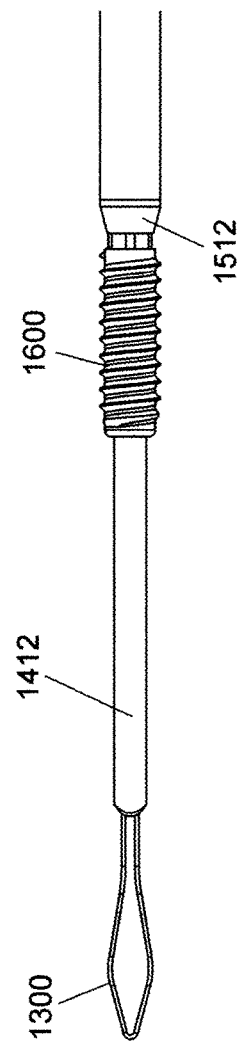
FIG. 3 is an expanded plan view of the elements of FIG. 2 at location A.
Figure 4:
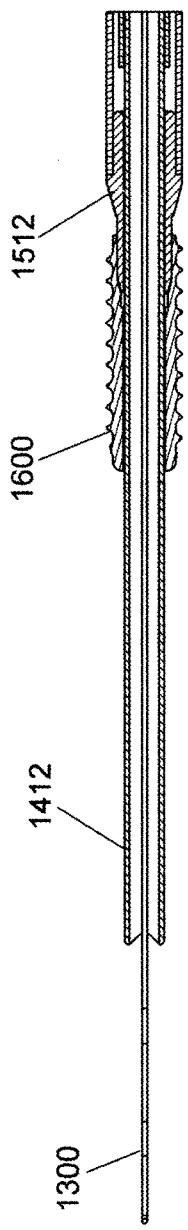
FIG. 4 is an expanded sectional view of the objects of FIG. 2 at location A-A.
Figure 7:
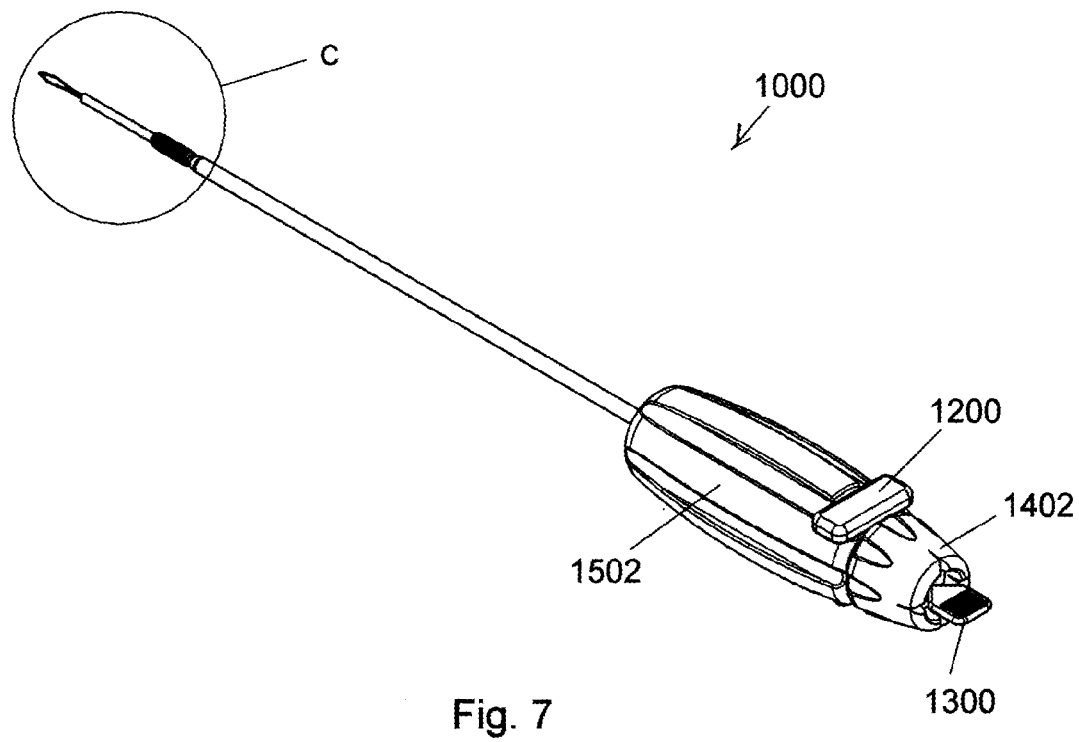
FIG. 7 is a perspective view of the objects of FIG. 2.
Figure 8:
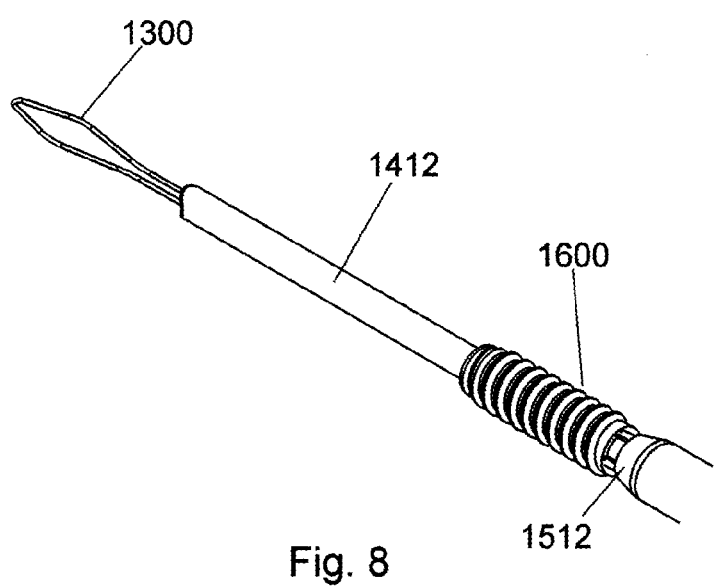
FIG. 8 is an expanded view of the objects of FIG. 7 at location C.
Figure 9:
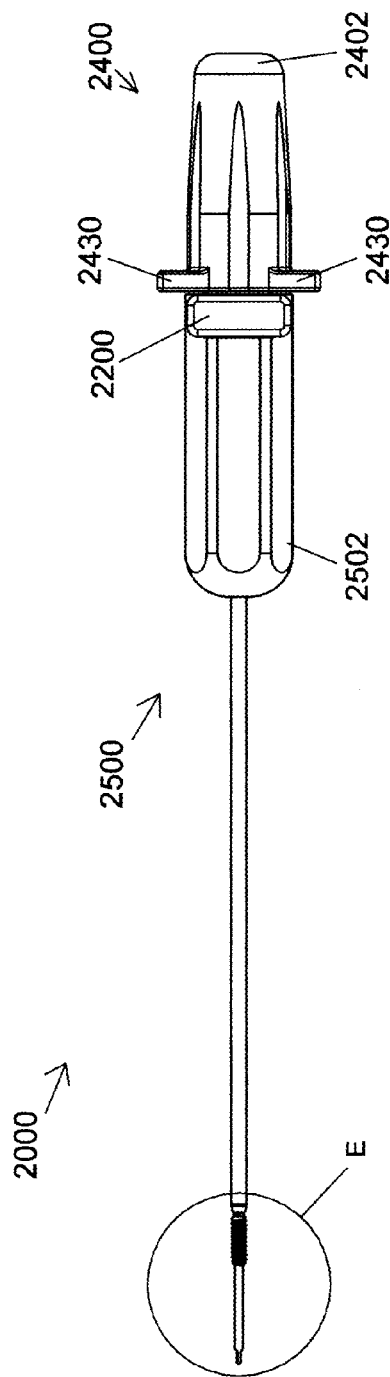
FIG. 9 is a perspective view of an exploded assembly of a second anchor placement system of the present invention.
Figure 10:
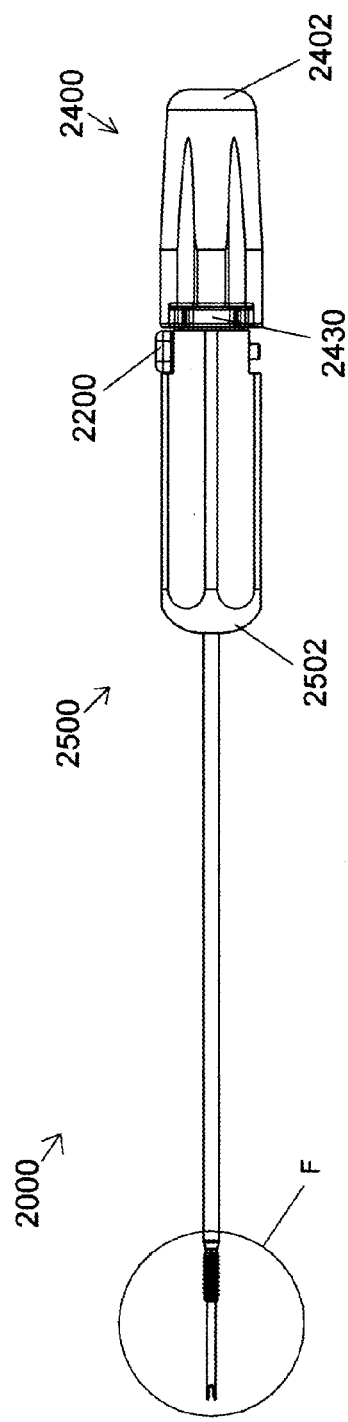
FIG. 10 is a side elevational view of the objects of FIG. 9.
Figure 11:
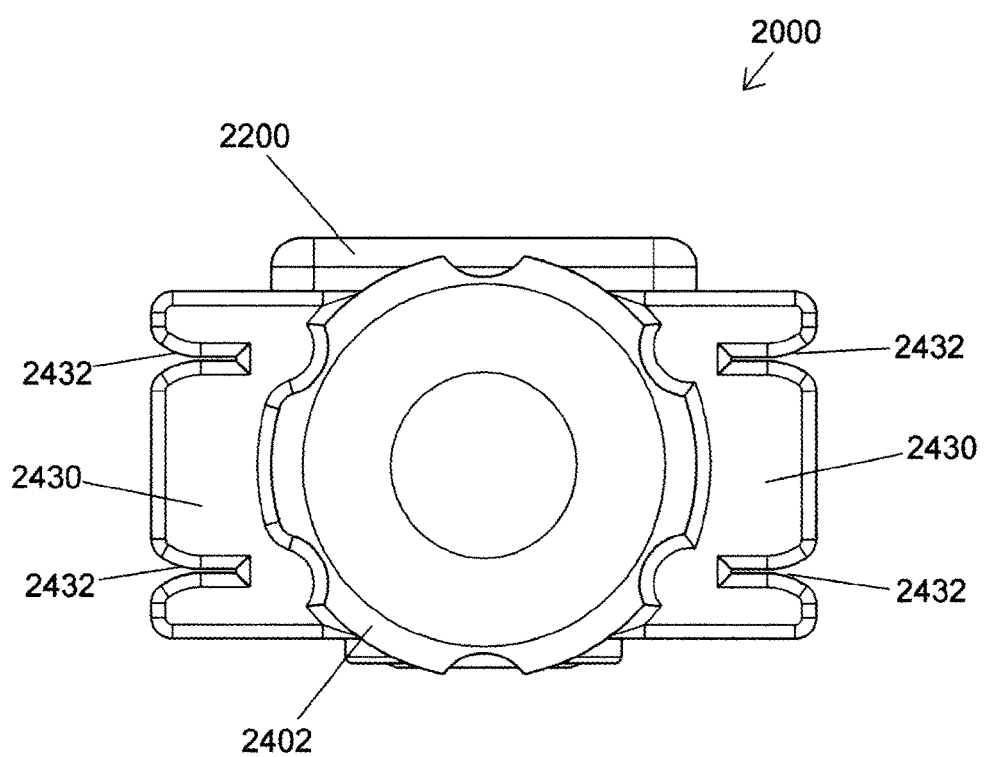
FIG. 11 is a proximal axial view of the objects of FIG. 9.
Figure 12:
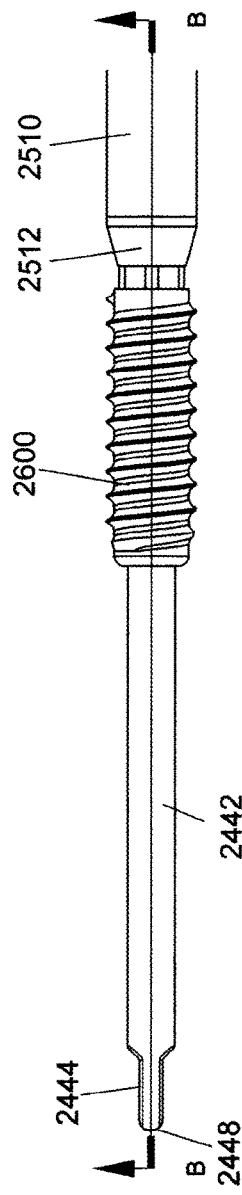
FIG. 12 is an expanded view of the distal portion of the objects of FIG. 9.
Figure 13:
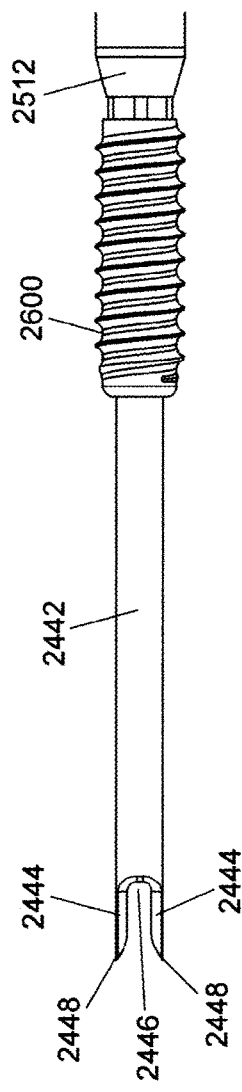
FIG. 13 is a plan view of the objects of FIG. 12.
Figure 14:
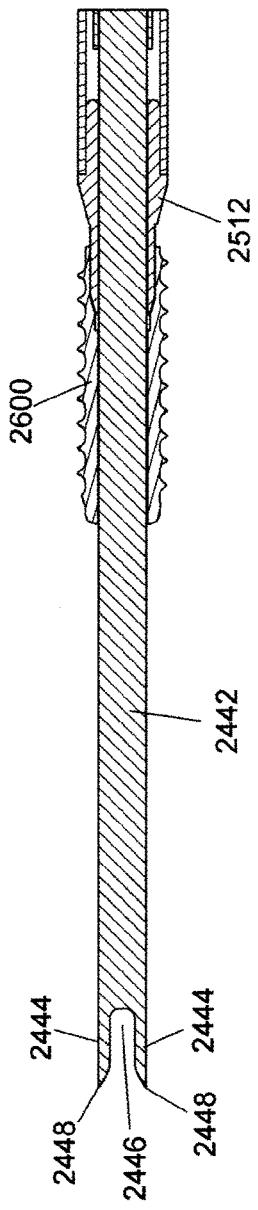
FIG. 14 is a sectional view of the objects of FIG. 12 at location B-B.
Figure 15:
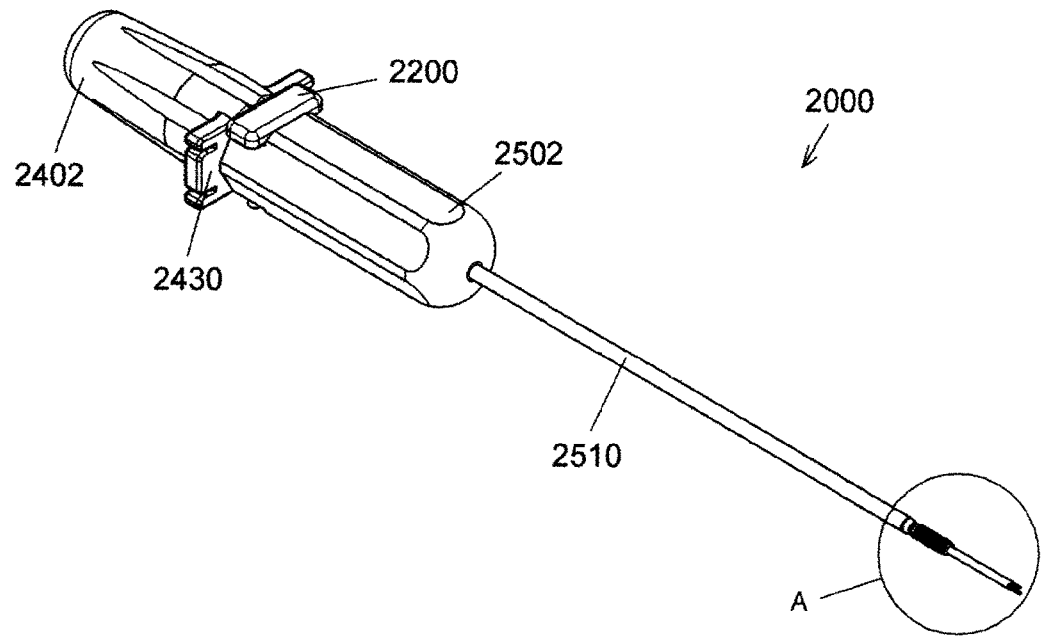
FIG. 15 is a distal perspective view of the objects of FIG. 9.
Figure 16:
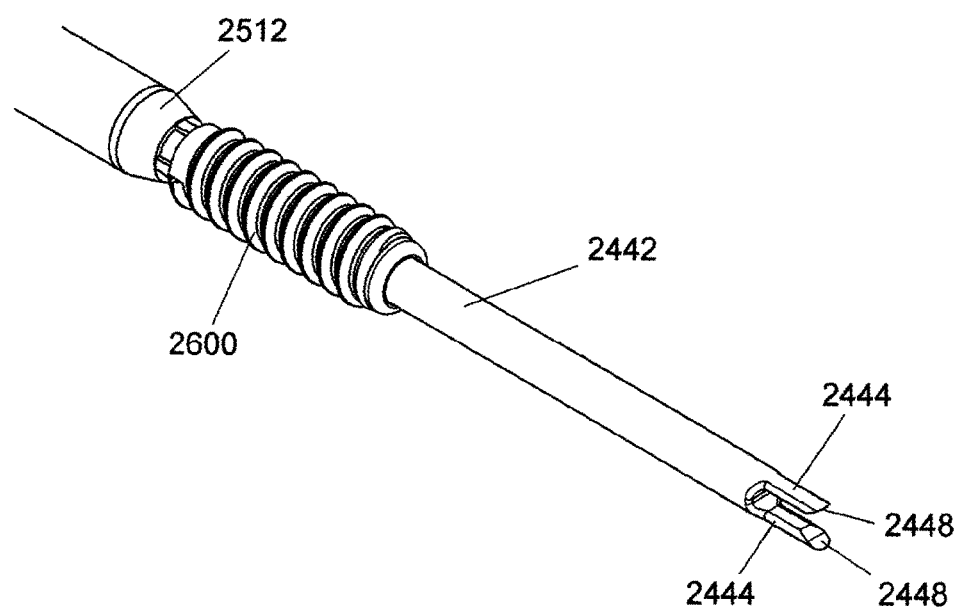
FIG. 16 is an expanded view of the objects of FIG. 15 at location A.
Figure 17:
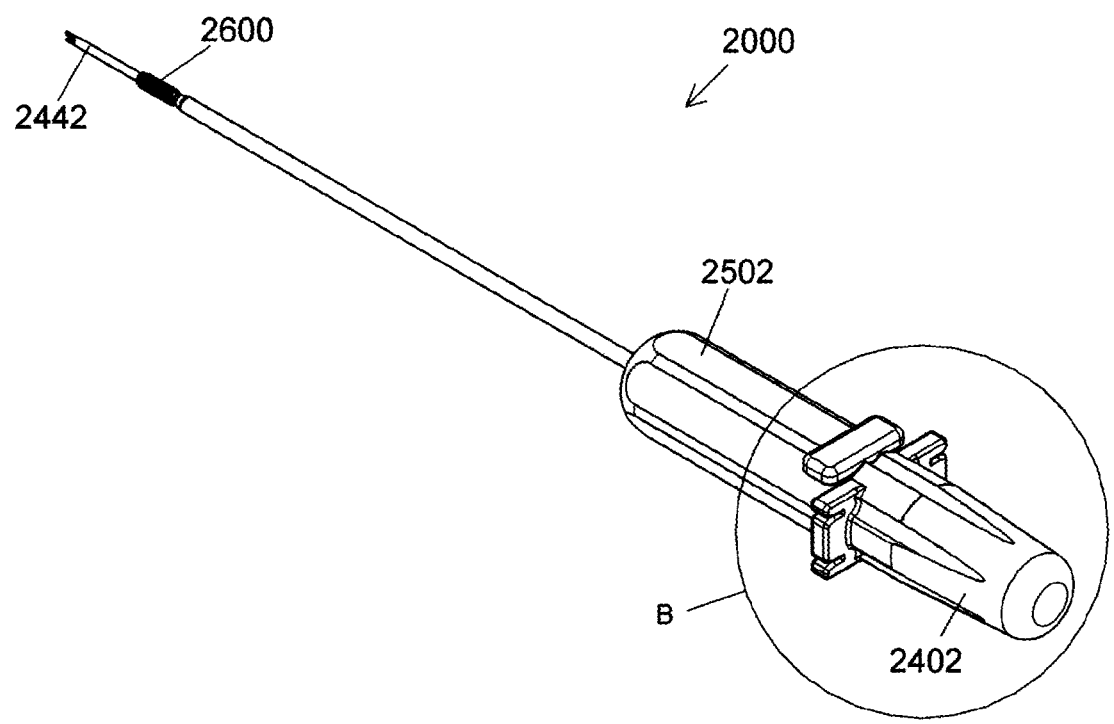
FIG. 17 is a proximal perspective view of the objects of FIG. 9.
Figure 18:
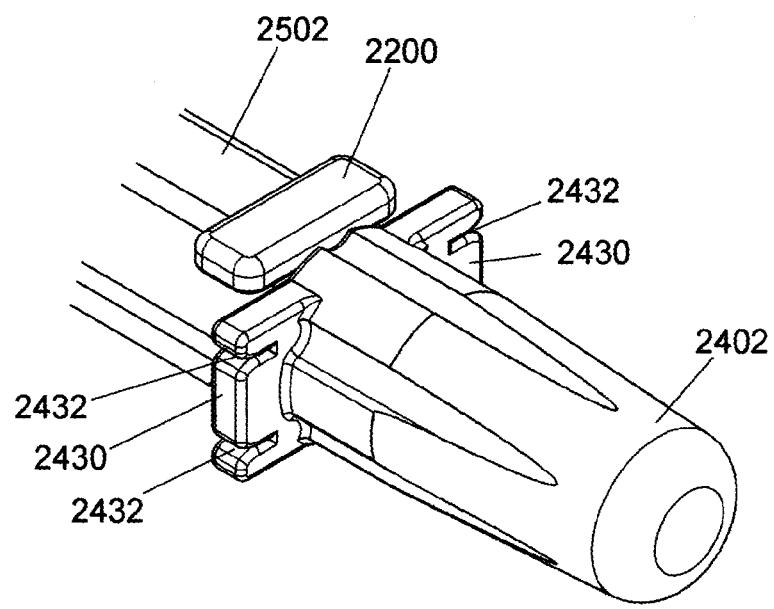
FIG. 18 is an expanded view of the objects of FIG. 17 at location B.

Aspects of the present invention relate to and/or overlap with aspects described in related co-pending and contemporaneously filed applications entitled "Ceramic Implant Placement Systems And Superelastic Suture Retention Loops For Use Therewith" Ser. No. 15/256,815 and "Implant Placement Systems And One-Handed Methods For Tissue Fixation Using Same" Ser. No. 15/256,838, the entire contents of which are hereby incorporated in their entirety.

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims. Accordingly, unless otherwise defined, all technical and scientific terms used herein have the same meaning as commonly understood by one of ordinary skill in the art to which the present invention belongs. However, in case of conflict, the present specification, including definitions below, will control.

In the context of the present invention, the following definitions apply:

The words "a", "an" and "the" as used herein mean "at least one" unless otherwise specifically indicated. Thus, for example, reference to an "opening" is a reference to one or more openings and equivalents thereof known to those skilled in the art, and so forth.

The term "proximal" as used herein refers to that end or portion which is situated closest to the user of the device, farthest away from the target surgical site. In the context of the present invention, the proximal end of the implant system of the present invention includes the driver and handle portions.

The term "distal" as used herein refers to that end or portion situated farthest away from the user of the device, closest to the target surgical site. In the context of the present invention, the distal end of the implant systems of the present invention includes components adapted to fit within the pre-formed implant-receiving socket.

In the context of the present invention, the terms "cannula" and "cannulated" are used to generically refer to the family of rigid or flexible, typically elongate lumened surgical instruments that facilitate access across tissue to an internally located surgery site.

The terms "tube" and "tubular" are interchangeably used herein to refer to a generally round, long, hollow component having at least one central opening often referred to as a "lumen".

The terms "lengthwise" and "axial" as used interchangeably herein to refer to the direction relating to or parallel with the longitudinal axis of a device. The term "transverse" as used herein refers to the direction lying or extending across or perpendicular to the longitudinal axis of a device.

The term "lateral" pertains to the side and, as used herein, refers to motion, movement, or materials that are situated at, proceeding from, or directed to a side of a device.

The term "medial" pertains to the middle, and as used herein, refers to motion, movement or materials that are situated in the middle, in particular situated near the median plane or the midline of the device or subset component thereof.

As discussed above, when a tissue, more particularly a soft connective tissue in a joint space, becomes damaged or torn from its associated bone or cartilage, surgery is usually required to reattach the tissue or reconstruct the bone. The present invention is directed to various means and mechanisms for securing the displaced tissue to boney tissue.

As used herein, the term "tissue" refers to biological tissues, generally defined as a collection of interconnected cells that perform a similar function within an organism. Four basic types of tissue are found in the bodies of all animals, including the human body and lower multicellular organisms such as insects, including epithelium, connective tissue, muscle tissue, and nervous tissue. These tissues make up all the organs, structures and other body contents. While the present invention is not restricted to any particular soft tissue, aspects of the present invention find particular utility in the repair of connective tissues such as ligaments or tendons, particularly those of the shoulder, elbow, knee or ankle joint.

In a similar fashion, while the present invention is not restricted to any particular boney tissue, a term used herein to refer to both bones and cartilage, aspects of the present invention find particular utility in the repair or reattachment of connective tissues to the boney elements of the shoulder, elbow, knee or ankle joint.

When the damaged tissue is of sufficient quantity and quality, the damaged portion may simply be directly reattached to the bone from which it was torn so that healing back to the bone can take place. However, in other situations, a "graft" may be needed to stimulate regrowth and permanent attachment. In the context of the present invention, the term "graft" refers to any biological or artificial tissue being attached to the boney tissue of interest, including:

Autografts, i.e., grafts taken from one part of the body of an individual and transplanted onto another site in the same individual, e.g., ligament graft;

Isografts, i.e., grafts taken from one individual and placed on another individual of the same genetic constitution, e.g., grafts between identical twins;

Allografts, i.e., grafts taken from one individual placed on genetically non-identical member of the same species; and Xenografts, i.e., grafts taken from one individual placed on an individual belonging to another species, e.g., animal to man.

Autografts and isografts are usually not considered as foreign and, therefore, do not elicit rejection. Allografts and xenografts are recognized as foreign by the recipient thus carry a high risk of rejection. For this reason, autographs and isografts are most preferred in the context of the present invention.

Surgical interventions such as contemplated herein generally require the boney tissue to be prepared for receiving the graft. In the context of the present invention, such preparation includes the formation of a "socket", i.e., a hole punched or drilled into the bone into which a prosthetic device such as an implant may be received. The socket may be prepared at the desired target location using conventional instruments such as drills, taps, punches or equivalent hole-producing devices.

While certain procedures contemplate directly attaching the graft to the bone, the more common route involves the employment of an implant specially configured to hold and/or enable attachment of the graft to the boney tissue. As used herein, the term "implant" refers to a prosthetic device fabricated from a biocompatible and/or inert material. In the context of the present invention, examples of such "implants" include conventional and knotless anchors of both the screw-threaded and interference-fit variety, as well as interference screws.

In certain embodiments, the present invention contemplates fabrication of the implant from either a metallic material or a suitable polymeric material, including, but not limited to, polyetheretherketone (PEEK), a polymeric composite such as, for instance, carbon fiber reinforced PEEK (PEEK CF), or of a suitable bioabsorbable material such as, for instance, polylactic acid (PLA). The present invention also contemplates the use of very small knotless anchors produced from ceramic materials using a process known as "Ceramic Injection Molding" or simply "CIM". The tensile strength of PEEK material is typically between 10,000 and 15,000 psi. In comparison, the tensile strength of alumina is generally in excess of 200,000 psi. Furthermore, recently developed materials such as Zirconia Toughened Alumina (ZTA) by Coorstek Inc. (Golden, Colo.) have a high degree of toughness in addition to high tensile strength. These materials, being ceramic, do not have a yield point and therefore do not deform under load. The high tensile strength and the absence of yielding under load of an implant constructed of such ceramic materials allow torque to be transmitted to the implant through features that are not producible by the machining of metal or that would fail in use if formed from a polymeric material such as PEEK.

In certain embodiments, the implant may take the form of a ceramic interference plug, wherein the high elastic modulus and high strength of the ceramic materials is beneficial for small and miniature interference type anchors that are driven axially into a prepared socket. The high modulus and high strength of the materials allows the thickness of the wall between the central lumen and the outer surface to be reduced compared to interference type anchors produced from polymeric materials without reducing the compressive force which retains the one or more sutures between the outer wall of the implant and the wall of the socket.

The preferred implant system of the present invention is comprised of an optionally cannulated tensioning device (also referred to as the "inserter" or "insertion device") slidably received within the lumen of a cannulated driver device (also referred to as the implant driver) that together serve to tension sutures in a prepared socket for the placement of a simple one-piece cannulated anchor. In the Examples below, the present invention makes reference to various lock-and-key type mating mechanisms that serve to establish and secure the axial and rotational arrangement of these device components. It will again be readily understood by the skilled artisan that the position of the respective coordinating elements (e.g., recessed slots and grooves that mate with assorted projecting protrusions, protuberances, tabs and splines) may be exchanged and/or reversed as needed.

The implant placement system of the present invention requires a robust connection between the "driver device" and the associated "implant" or "anchor" so as to ensure that the two rotate as a single unit such that rotational force or "torque" applied to the proximal end of the system (e.g., via the proximal handle portion of the driver device) is transmitted to the distal end of the system (e.g., the distal end of the implant disposed in the prepared socket) without incident or interruption. This continuous "torque transfer" along the length of the system, from proximal to distal end, is critical to the function of the driver, enabling it to distally advance the implant and firmly secure the implant (and any associated sutures or tissues) in the biological site of interest. In the context of the present invention, this continuous torque transfer is achieved by means of coordinating "torque-transmitting" elements, namely a distal "torque-transmitting portion" of the driver device that is configured to mate with and/or conform to a "torque-transmitting" (or alternatively "torque-receiving" or "torque-transferring") portion of the implant, such "portion" including at a minimum the proximal end of the implant though the present invention contemplates embodiments where "torque-trans-mitting" features on the implant extend along the length of the implant. The respective "torque-transmitting" features on the driver device and implant cooperate to ensure that any proximal torque applied by the user to the proximal handle portion of the device is directly conveyed ("transmitted") to the distal end of the implant.

In certain embodiments, the torque-transmitting portion of the implant may take the form of a laterally extending slot in the proximal end of the implant similar to a standard screwdriver slot; however, other geometries are contemplated and described in detail herein as well as in disclosures incorporated by reference herein. In addition, like the implant itself, the distal torque-transmitting portion of the driver may also be fabricated from a ceramic material and formed by ceramic injection molding so as to allow miniaturization of the torque-transmitting features.

The present invention makes reference to insertion devices commonly referred to in the art as "drills" and "drivers", i.e., devices that "drill" the socket and "drive" the implant into the socket. In the context of the present invention, the drills and drivers may be conventional, e.g., rigidly linear as previously herein described, or, as discussed in detail herein, "off-axis", e.g., having an angularly offset distal portion adapted to drill off-axis sockets in boney tissues that are remote and difficult to access and drive therein the corresponding implant, such as an anchor or interference screw.

The present invention contemplates securing the graft to the implant via sutures. In the context of the present invention, the term "suture" refers to a thread-like strand or fiber used to hold body tissues after surgery. Sutures of different shapes, sizes, and thread materials are known in the art and the present invention is not restricted to any particular suture type. Accordingly, in the context of the present invention, the suture may be natural or synthetic, monofilament or multifilament, braided or woven, permanent or resorbable, without departing from the spirit of the invention.

In certain embodiments, the present invention makes reference to an elongate element of a superelastic and/or shape memory material configured to include a suture retention loop at its distal end and designed to be slidably received within a lumen of a cannulated tensioning device or inserter. In certain preferred examples, the elongate element takes the form of a "nitinol wire". In the context of the present invention, "nitinol" is a super elastic metal alloy of nickel and titanium. In a preferred embodiment, the two elements are present in roughly equal atomic percentage (e.g., Nitinol 55, Nitinol 60). Nitinol alloys exhibit two closely related and unique properties: shape memory effect (SME) and superelasticity (SE; also called pseudoelasticity, PE). Shape memory is the ability of nitinol to undergo deformation at one temperature, then recover its original, undeformed shape upon heating above its "transformation temperature". Superelasticity occurs at a narrow temperature range just above its transformation temperature; in this case, no heating is necessary to cause the undeformed shape to recover, and the material exhibits enormous elasticity, some 10-30 times that of ordinary metal.

The present invention also makes reference to high strength polymeric materials and high tensile strength ceramic materials, such as alumina or zirconia, that may be formed to complex shapes by a process referred to as Ceramic Injection Molding (CIM). In this process, ceramic powder and a binder material are molded to a shape that is subsequently fired in a furnace to eliminate the binder material and sinter the ceramic powder. During this sintering operation the item is reduced in size by twenty to thirty percent and achieves near 100% density with very high dimensional repeatability. Ceramic materials that are routinely molded and thus contemplated by the present invention include, but are not limited to, alumina, zirconia toughened alumina (ZTA) and partially stabilized zirconia (PSZ). The flexular strengths of these materials range from 55,000 psi to 250,000 psi, far higher than the 25,000 psi flexular strength of implantable PEEK material.

The instant invention has both human medical and veterinary applications. Accordingly, the terms "subject" and "patient" are used interchangeably herein to refer to the person or animal being treated or examined. Exemplary animals include house pets, farm animals, and zoo animals. In a preferred embodiment, the subject is a mammal, more preferably a human.

Hereinafter, the present invention is described in more detail by reference to the Figures and Examples. However, the following materials, methods, figures, and examples only illustrate aspects of the invention and are in no way intended to limit the scope of the present invention. For example, while the present invention makes specific reference to arthroscopic procedures, it is readily apparent that the teachings of the present invention may be applied to other minimally invasive procedures and are not limited to arthroscopic uses alone. As such, methods and materials similar or equivalent to those described herein can be used in the practice or testing of the present invention.

EXAMPLES

FIG. 1 depicts driver 1500 with anchor 1600 loaded thereto, tensioning (insertion) device 1400 with loading loop 1300 positioned for loading a suture, and key 1200 prior to mounting of driver 1500 to tensioning device 1400 in preparation for use. When driver 1500 is mounted to tensioning device 1400, off-axis slots 1406 of handle 1402 of tensioning device 1400 are aligned with off-axis holes 1506 of handle 1502 of driver 1500 and cylindrical portions of key 1200 are inserted into the passages so formed. Positioning of key 1200 in this manner prevents axial and rotational movement of tensioning device 1400 relative to driver 1500. FIGS. 2 through 8 depict knotless suture anchor system 1000 of the instant invention prepared for use with key 1200 and loading loop 1300 in place. Distal tubular element 1412 of tensioning device 1400 extends distally beyond anchor 1600 and distal driving element 1512 of driver 1500. Detailed descriptions of the construction and use of placement system 1000 are contained in U.S. Pat. No. 9,226,817 the contents of which are incorporated herein by reference in their entirety.

FIGS. 9 through 18 depict a second implant placement system 2000 of the present invention having construction like that of placement system 1000. That is, non-rotating tensioning device 2400 located within the cannulation of driver 2500 is used to tension one or more sutures prior to the placement of anchor 2600. Placement system 2000 is identical to system 1000 in all aspects except as specifically subsequently described. For example, cannulated distal tubular element 1412 of system 1000 may be replaced by distal element 2442 which is not cannulated and has formed at its distal end elongate laterally opposed, distally extending portions 2444 with sharpened distal ends 2448. Elongate portions 2444 form the tines of a fork with channel 2446 formed between portions 2444. Tensioning device handle 2402 has formed near the distal end of its external surface flanges 2430 wherein are formed slots 2432 which serve as cleats for maintaining the tension of sutures placed therein, flanges 2430 and slots 2432 replacing slots 1408 in hub 1402 of system 1000. The construction and use of placement system 1000 is described in detail in parent application Ser. No. 15/012,060 filed Feb. 1, 2016, Ser. No. 14/972,662 filed Dec. 17, 2015, and Ser. No. 14/636,389 filed Mar. 3, 2015, the contents of which have been previously incorporated herein by reference in their entirety.

During use, distal element 2412 of tensioning device 2400 is inserted into a prepared socket in which anchor 2600 is to be placed. Sutures are retained in gap 2446 between distally extending portions 2444 of distal element 2442 and may be tensioned and cleated in slots 2432 in handle 2402 of tensioning device 2400. Thereafter, driver 2500 is uncoupled from tensioning device 2400 by the removal of key 2200. Anchor 2600 is then advanced to the socket and threaded into place while the tension and graft position are maintained by tensioning device 2400.

Figure 19:
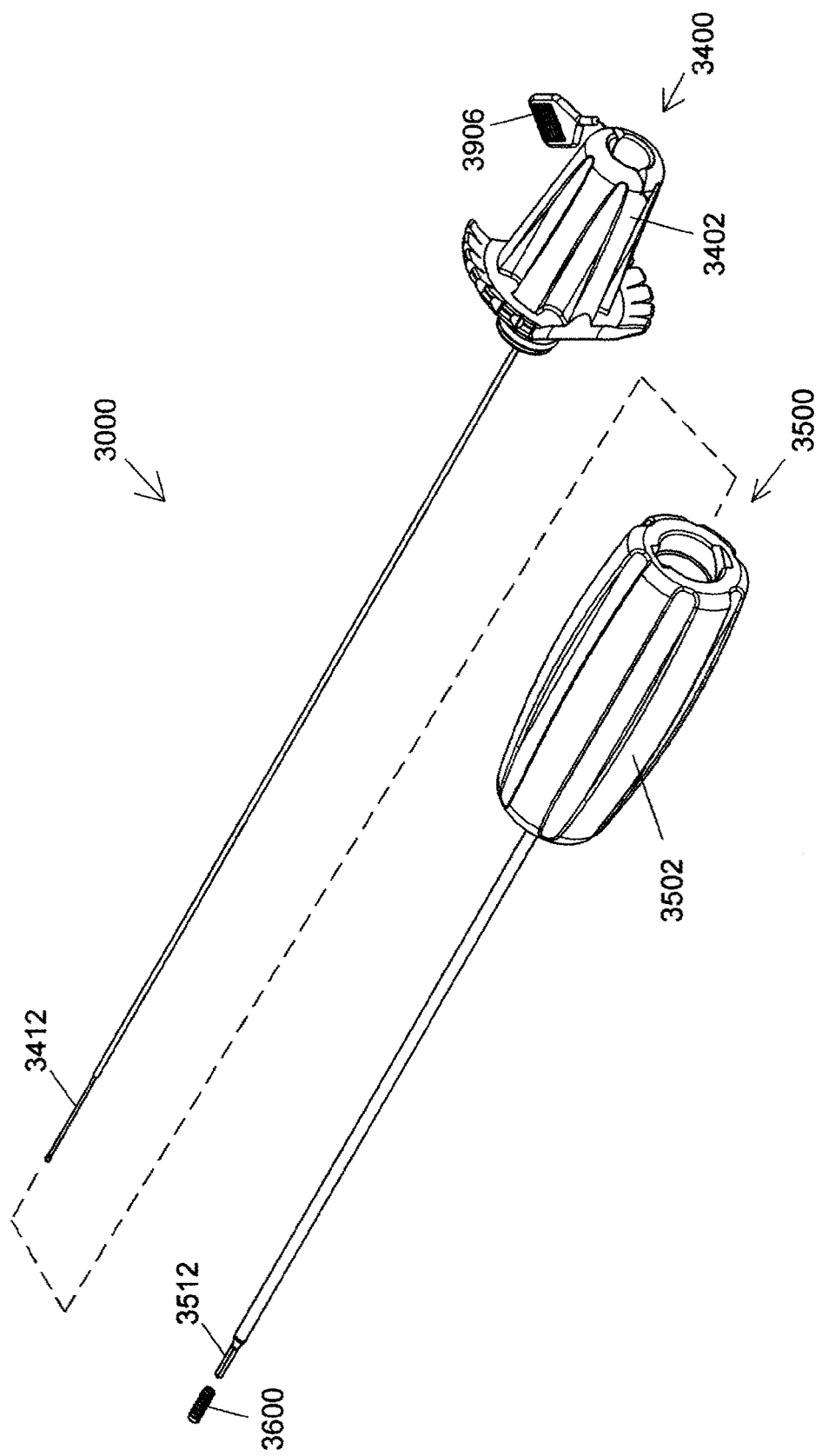
FIG. 19 is a perspective view of an exploded assembly of a third anchor placement system of the present invention.
Figure 20:
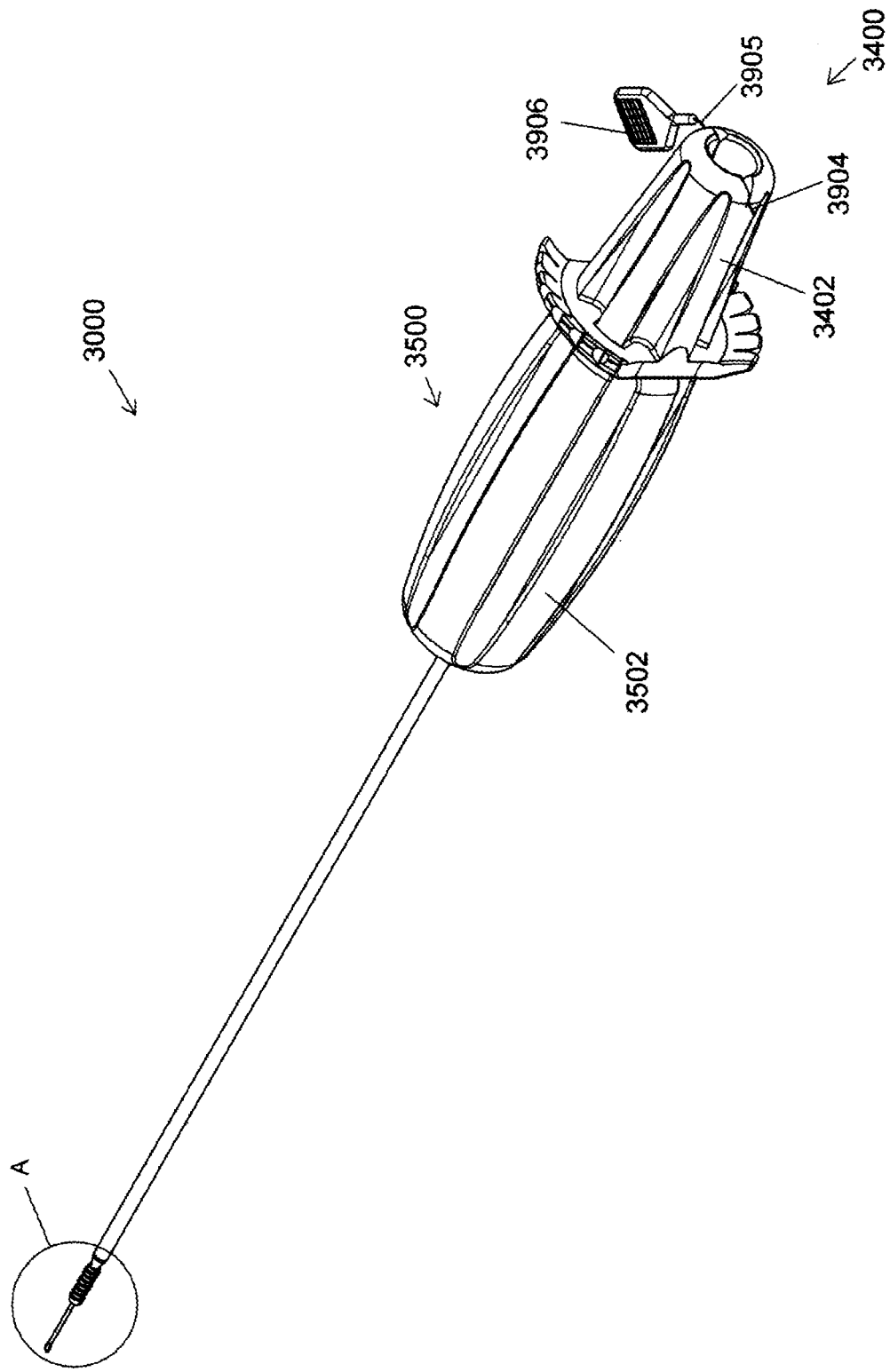
FIG. 20 is a perspective view of the assembled anchor placement system of FIG. 19.

Implant placement system 3000, depicted as an exploded assembly of tensioning/insertion device 3400, driver 3500 and anchor 3600 in FIG. 19 is configured for the placement of small diameter cannulated implants. The elongate distal portion of tensioning device 3400 is rotatably and slidably positioned within the cannulation of driver 3500. Handles/hubs 3402 and 3502 of tensioning device 3400 and 3500 respectively are removably coupled.

Figure 21:
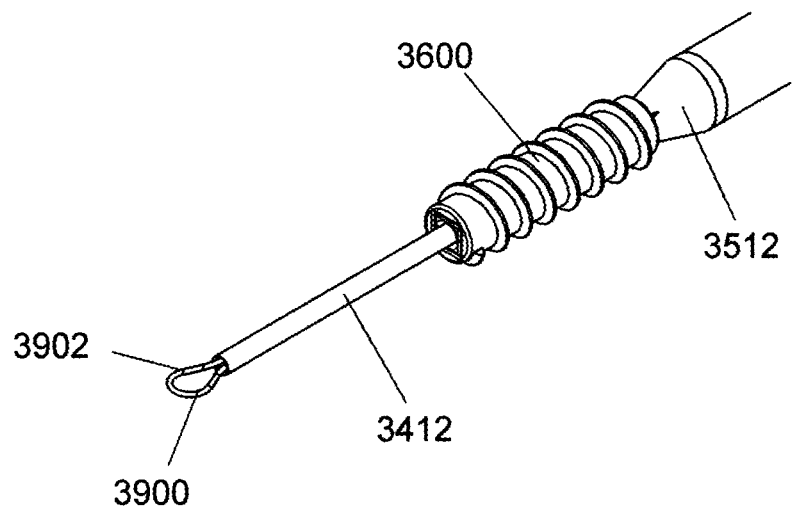
FIG. 21 is an expanded distal perspective view of the distal portion of the anchor placement system of FIG. 20.
Figure 22:
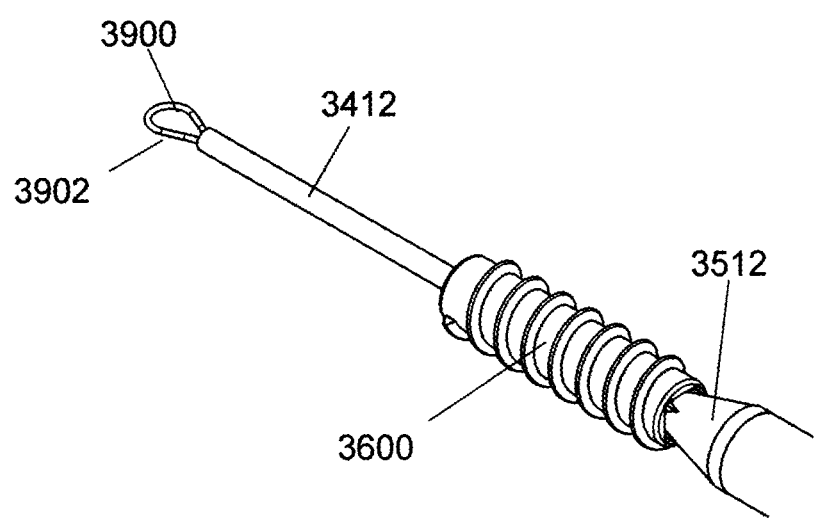
FIG. 22 is an expanded proximal perspective view of the distal portion of the anchor placement system of FIG. 20.
Figure 23:
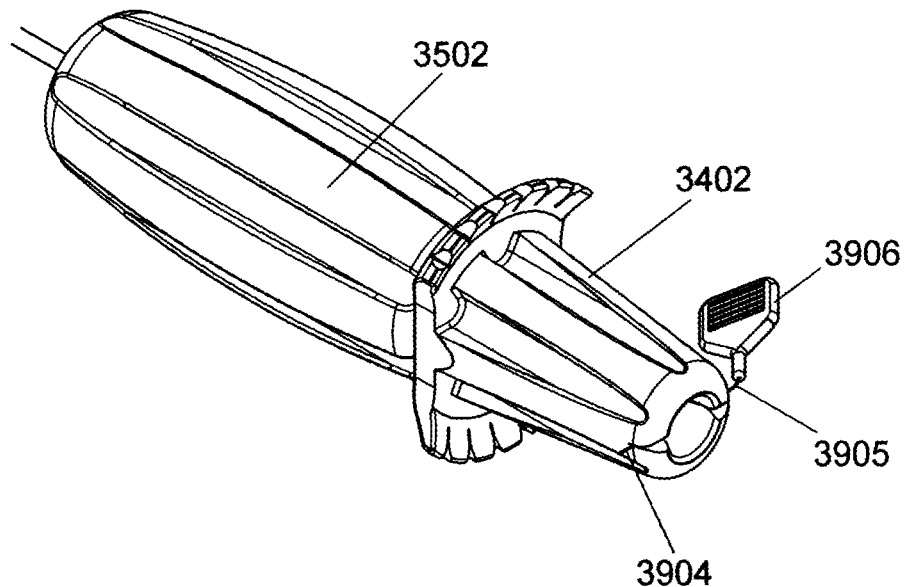
FIG. 23 is an expanded proximal perspective view of the proximal portion of the anchor placement system of FIG. 20.
Figure 24:
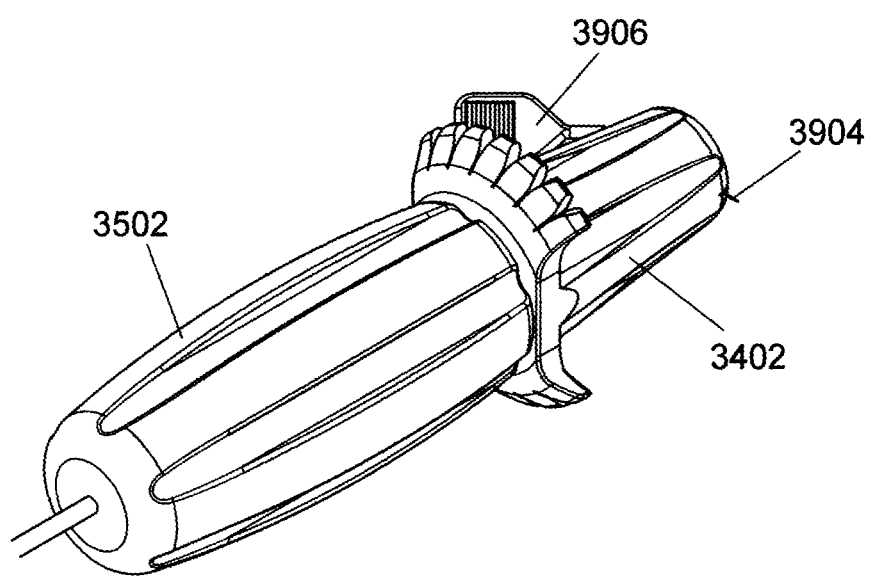
FIG. 24 is an expanded distal perspective view of the proximal portion of the anchor placement system of FIG. 20

FIGS. 20 through 24 depict implant placement system 3000 assembled and ready for use. As shown in FIG. 21, cannulated distal element 3412 of tensioner/inserter 3400 protrudes distally beyond distal drive element 3512 and anchor 3600 removably mounted thereon. The distal portion of elongate element 3900 forms a loop 3902 adjacent to the distal end of cannulated distal element 3412 of inserter 3400. Second proximal end 3904 and first proximal end 3905 of elongate element 3900 are removably secured (cleated) in slots/cleats 3405, pull-tab 3906 being affixed to a first end 3905 of elongate element 3900.

Figure 25:
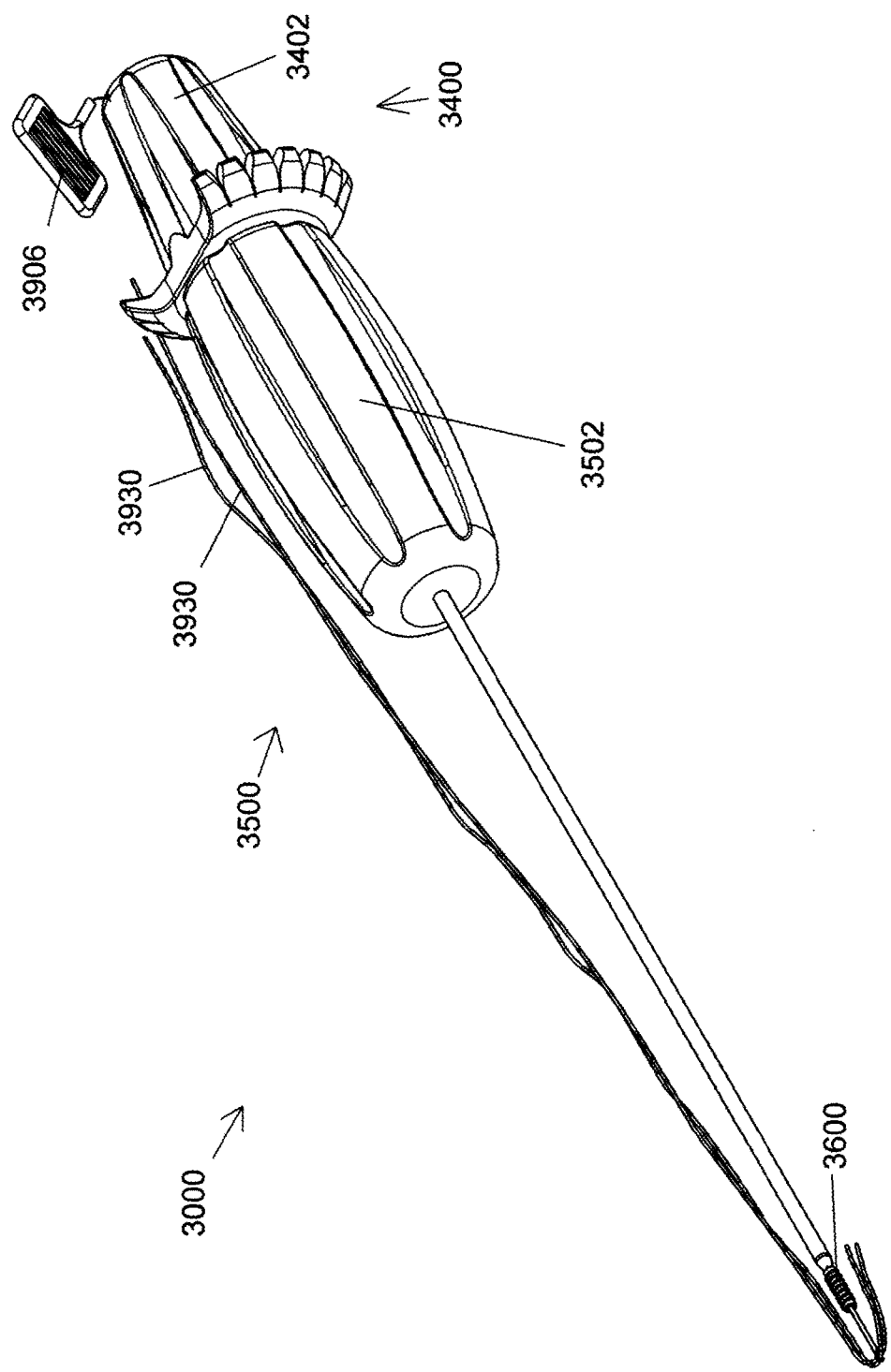
FIG. 25 is a perspective view of the anchor placement system of FIG. 20 with suture loaded in preparation for use.
Figure 26:
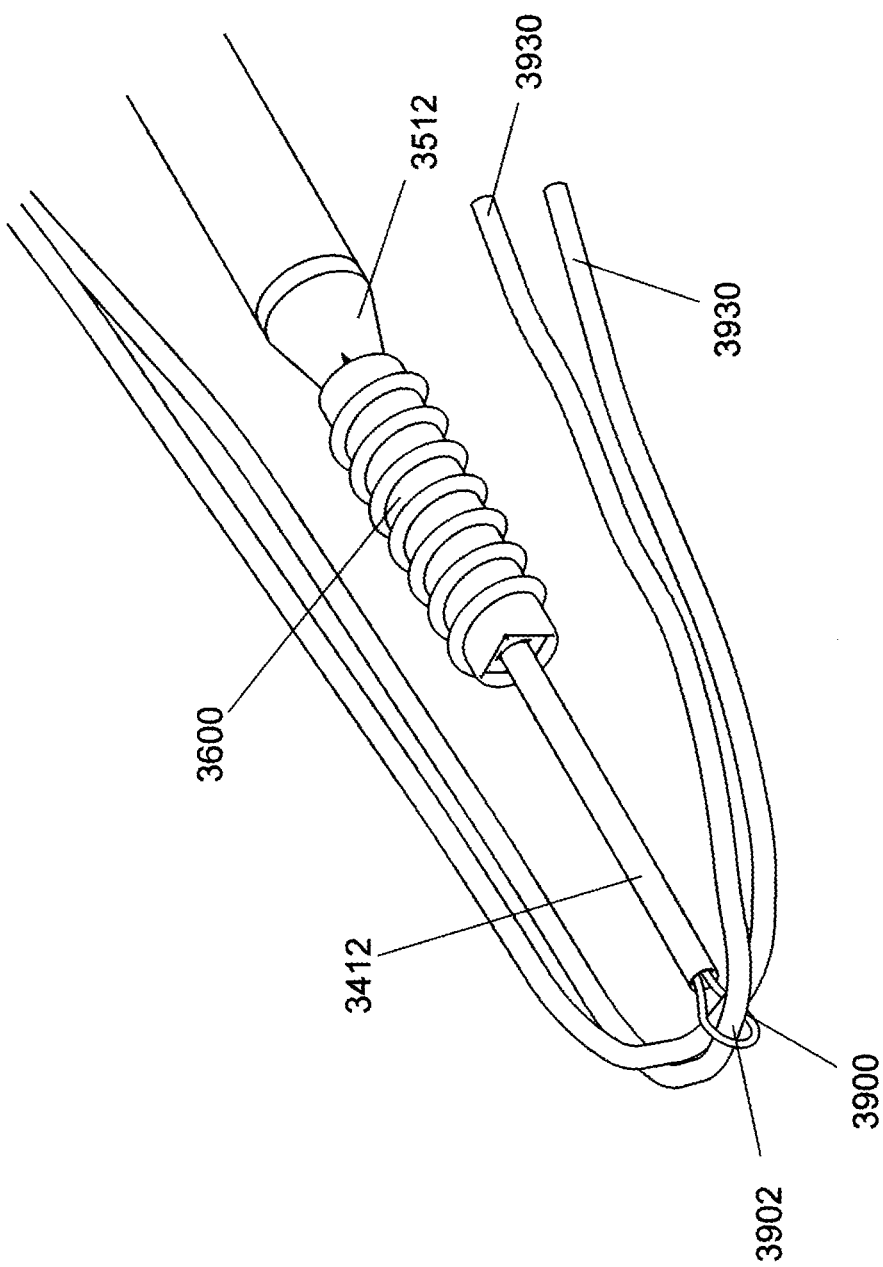
FIG. 26 is an expanded view of the distal portion of the anchor placement system of FIG. 25.
Figure 27:
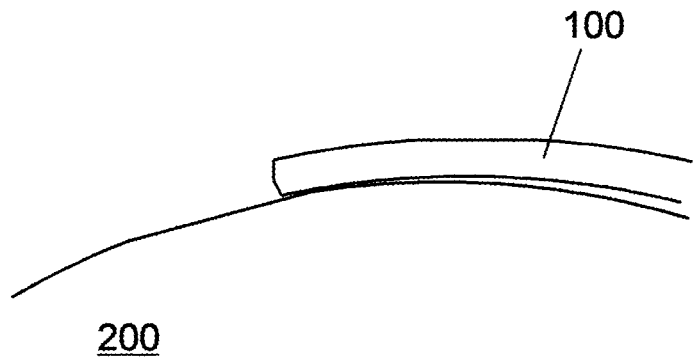
FIG. 27 is a diagrammatic representation of a graft and bone from which the graft has been separated as in a rotator cuff tear.
Figure 28:
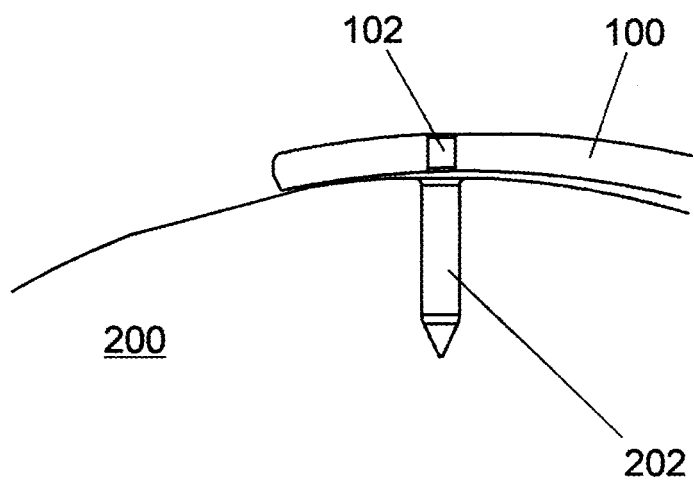
FIG. 28 depicts the graft and bone of FIG. 27 with a first medial socket suitable for the placement of an anchor formed in the bone.

An illustrative example of a method for affixing a graft to a boney surface, as in repairing a torn rotator cuff or other tendon insertion onto a bony surface, is depicted in FIGS. 27 through 38. FIG. 27 depicts a graft 100 that has separated from the surface of bone 200. The region in which graft 100 is to be reattached to the surface of bone 200 is prepared by abrading with an arthroscopic burr or shaver. Thereafter, as depicted in FIG. 28, a socket 202 is formed in bone 200 in a selected location beneath cuff 100, forming an opening 102 in graft 100. Suture 300 is loaded into the distal loop 3902 of anchor system 3000 as depicted in FIGS. 25 and 26.

Alternatively, anchor placement systems 1000 or 2000 could be substituted for system 3000, the choice being one of practioner preference. Anchor system 3000 is selected for this medial anchor because, due to its small diameter, the area for reattachment of graft 100 to bone 200 is minimally reduced by socket 202. In this example, a single suture 300 is used to illustrate the method for placing an anchor and tensioning a suture to affect a rotator cuff repair in accordance with the principles of the present invention. However, frequently a repair construct employing multiple sutures 300 is needed to secure the graft to the boney surface. In the context of the present invention, anchor placement system 3000 is able to secure multiple sutures with a small diameter anchor due to its unique construction and is, therefore, well-suited to placement in locations beneath the soft tissue (medial placement).

Figure 29:
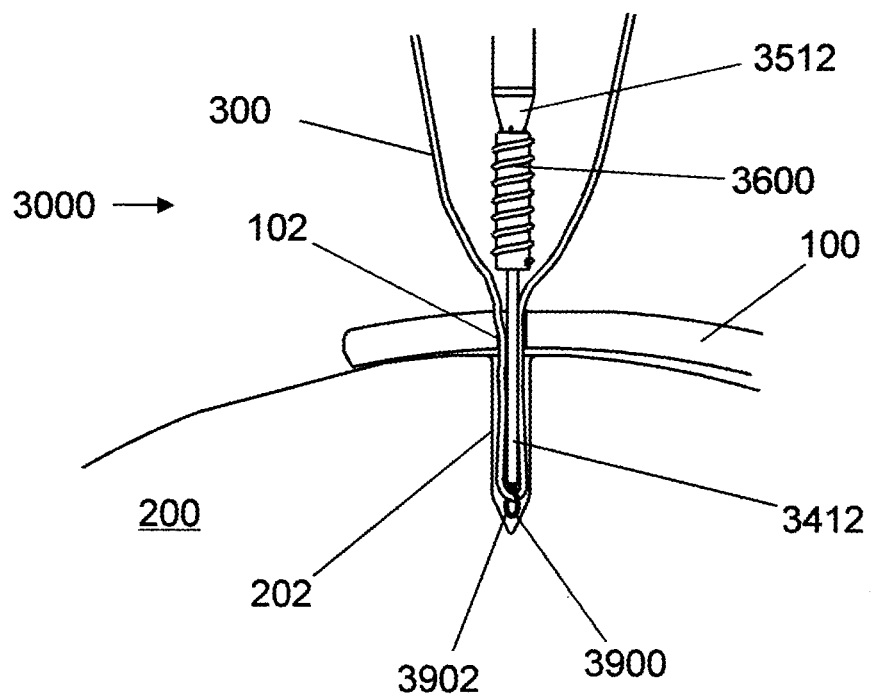
FIG. 29 depicts the graft and bone of FIG. 28 with the distal portion of the anchor placement system of FIG. 19 inserted into the first medial socket in preparation for the placement of a first tissue anchor.
Figure 30:
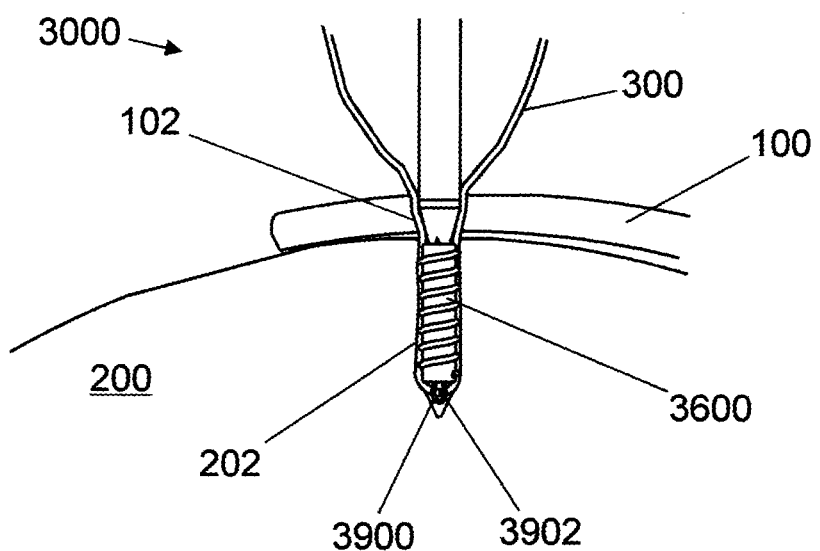
FIG. 30 depicts the elements of FIG. 29 wherein a first anchor has been placed in the first medial socket so as to affix a suture thereto.
Figure 31:
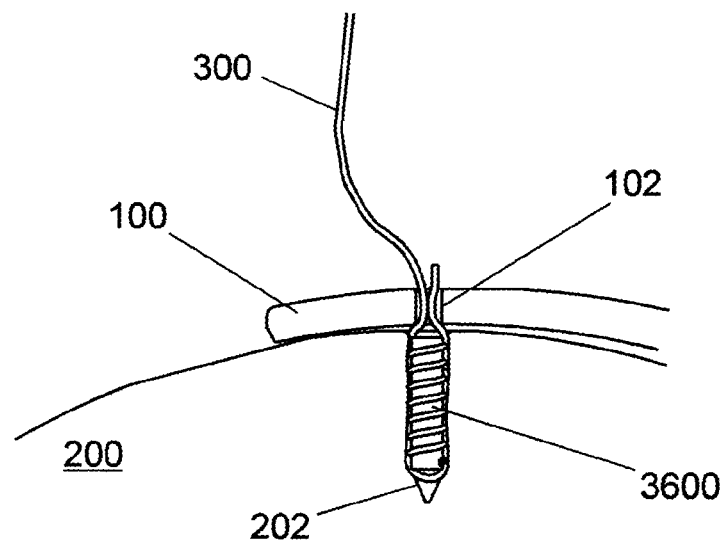
FIG. 31 depicts a suture affixed to the bone by a first anchor placed in a first socket.
Figure 32:
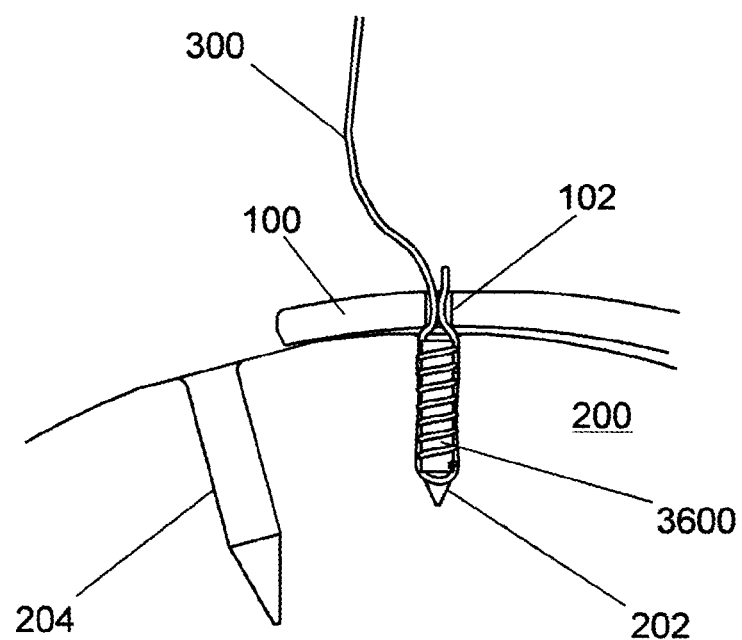
FIG. 32 depicts the objects of FIG. 31 wherein a second lateral socket suitable for placement of an anchor therein has been formed in the bone.
Figure 33:
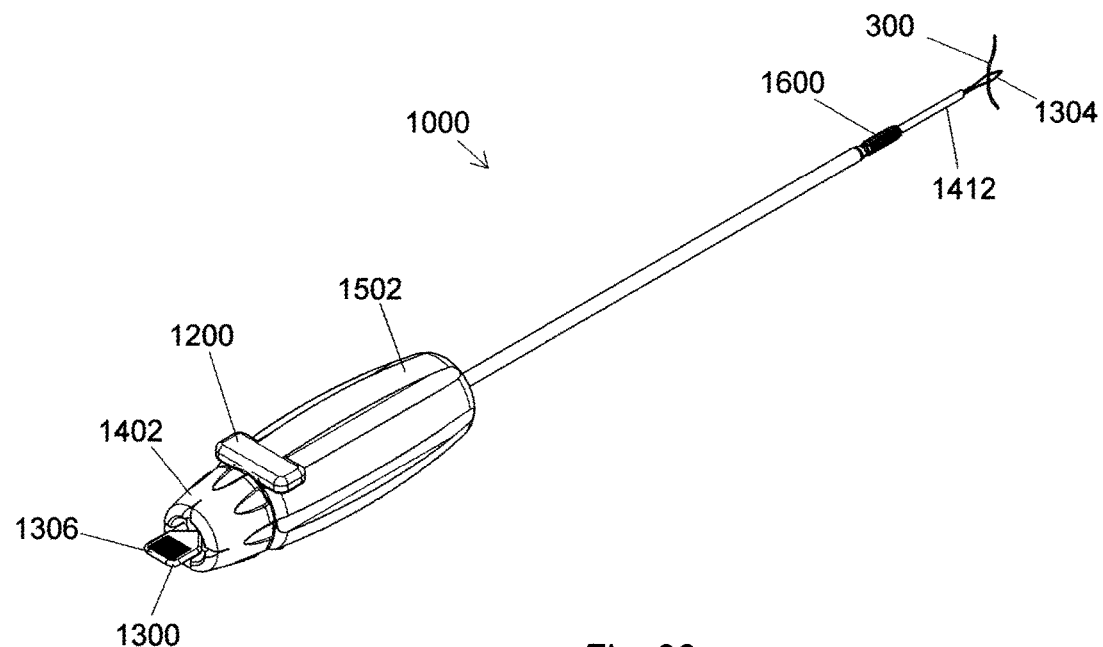
FIG. 33 is a proximal perspective view of the anchor placement system of FIG. 19 wherein the suture previously affixed to the bone by the first medial anchor is prepared for loading into the anchor placement system.
Figure 34:
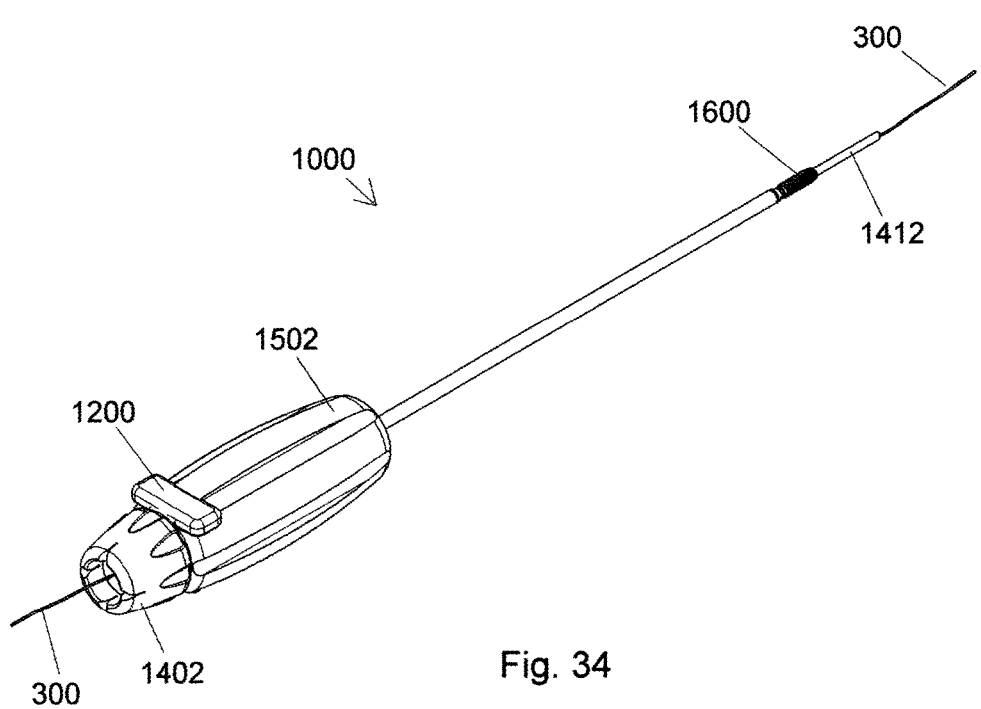
FIG. 34 is a proximal perspective view of the objects of FIG. 33 wherein the suture is loaded into the suture placement system.
Figure 35:
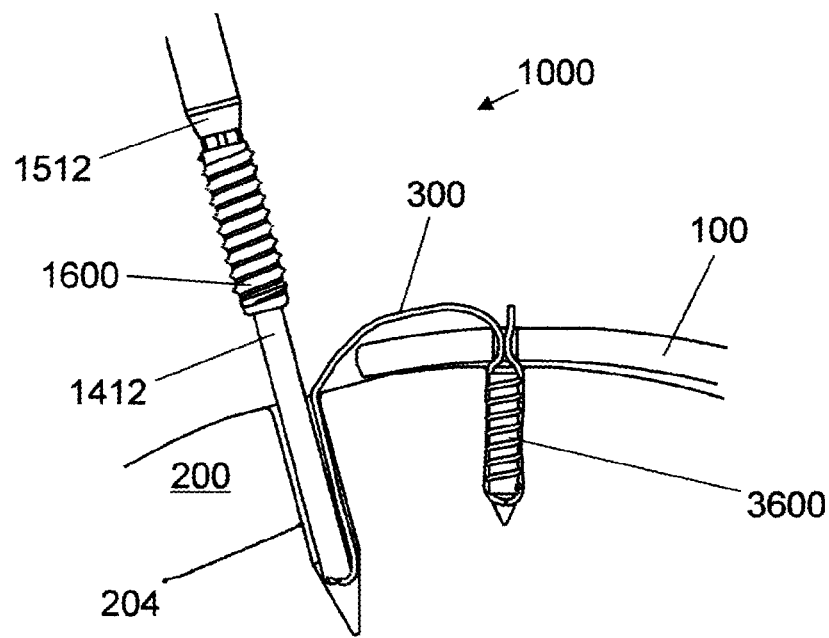
FIG. 35 depicts the elements of FIG. 32 wherein the distal portion of the first anchor placement system of FIG. 2 is inserted into the second lateral socket in preparation for tensioning of the suture for anchor placement.
Figure 36:
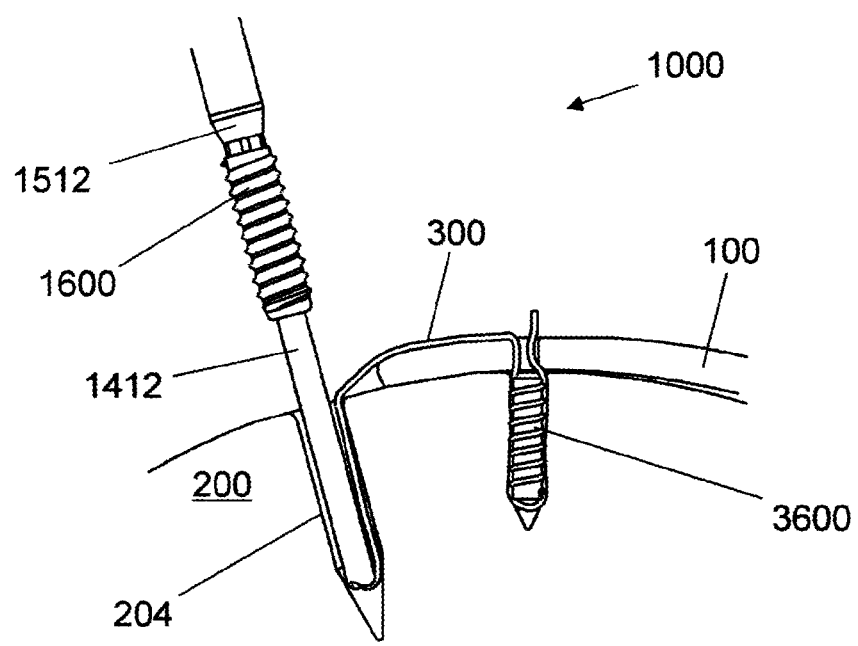
FIG. 36 depicts the objects of FIG. 35 wherein the suture has been tensioned in preparation for anchor placement.
Figure 37:
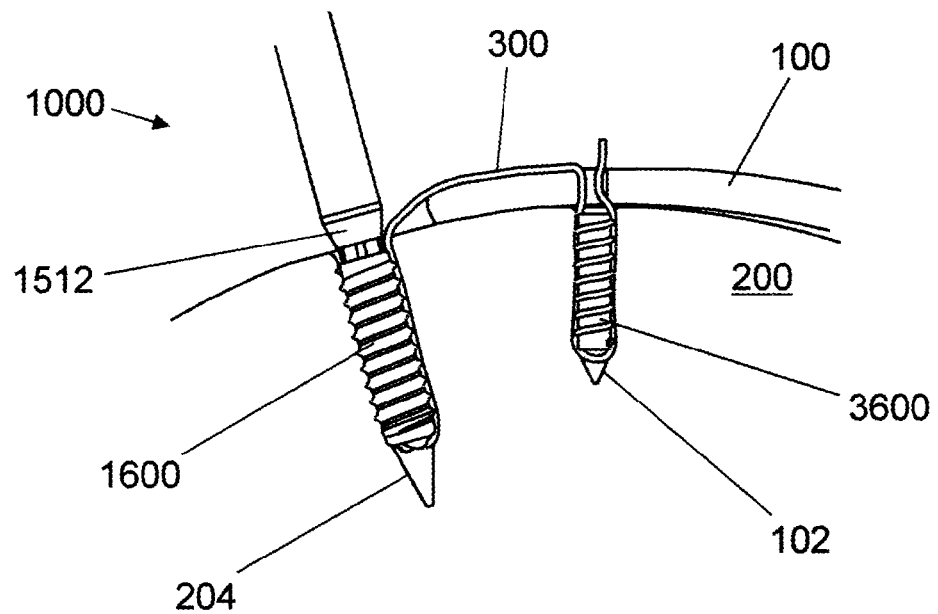
FIG. 37 depicts the objects of FIG. 36 wherein the anchor has been placed in the second lateral socket so as to affix the suture to the bone.
Figure 38:
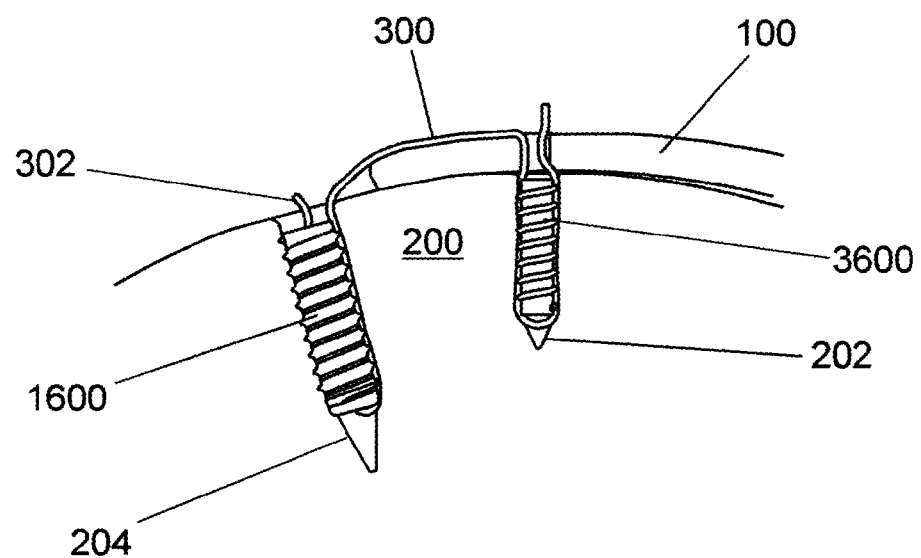
FIG. 38 depicts a completed construction in which a portion of a graft is retained against a boney surface by a tensioned suture extending between a first medial anchor and a second lateral anchor in accordance with the principles of the present invention.

Referring now to FIG. 29, distal element 3412 with loop 3902 of elongate element 3900 and suture 300 positioned therein (see FIGS. 25 and 26) is inserted into socket 202. Thereafter, as depicted in FIG. 30, anchor 3600 is threaded into socket 202 so as to secure suture 300 between the threaded outer surface of anchor 1600 and the sidewall of socket 200. Elongate element 3900 is then removed and placement system 3000 is withdrawn from the site. One suture tail may be trimmed as depicted in FIG. 31 or trimmed at the completion of the construct. Socket 204 may then be formed in bone 200 in a position lateral to cuff 100 as shown in FIG. 32. Suture 300 is then loaded into anchor system 1000 as depicted in FIGS. 33 and 34 using loading loop 1304. Distal element 1412 of system 1000 may be inserted into socket 204 as depicted in FIG. 35 and tensioned as shown in FIG. 36 by pulling on the portion of suture 300 proximal to handle 1402 of tensioning device 1400 and cleated in the slots provided so as to maintain the tension. Anchor 1600 may then be screwed into place thereby trapping suture 300 between the threaded outer surface of anchor 1600 and the wall of socket 204 as shown in FIG. 37. Suture 300 is then uncleated from handle 1402 of insertion device 1400, placement system 1000 is removed from the site, and suture tail 302 is trimmed as shown in FIG. 38. Soft tissue 100 is pressed against bone 200 by suture 300 extending from medial anchor 3600 to lateral anchor 1600.

In this example, anchor system 1000 was used for the lateral suture. However, anchor placement systems 2000 or 3000 could readily be used instead as the choice of a particular system is one of practioner preference. All of the inventive systems allow the tensioning of suture 300 prior to anchor placement. In addition, in contrast to other knotless anchor systems, if, after anchor placement, the tension in suture 300 is found to be more or less than intended, anchor 1600 (or 2600 or 3600) can be backed out, the sutures retensioned, and the anchor threaded into socket 204 again. This is possible because the anchor system uses a single implant to secure the suture by trapping the suture between the implant and one or more regions of the socket wall. This stands in stark contract to prior art systems that use a first distal implant secured in place by a second proximal implant in the same prepared socket, or by an implant to which one or more sutures is fixed secured by a second, engaging element.

In the example above, a single strand of suture 300 between a single medial anchor 3600 and a single lateral anchor 1600 compresses a portion of graft 100 against a prepared surface of bone 200. While this is sufficient for very small tears, for larger tears, it is frequently advantageous to retain the graft in its position against the prepared boney surface using a matrix of medial and lateral anchors with tensioned sutures between anchors of the matrix. This method is known as a "double row" technique because it involves a medial "row" of anchors and a lateral "row" of anchors, the "rows" generally each having two or more anchors. Tensioning between these adjacent anchors and the fixation of the sutures in the sockets by implants is accomplished in the manner previously herein described. Each implant may affix multiple strands of suture; however, in accordance with the principles of the present invention, each individual strand of suture may be individually tensioned and that tension maintained unchanged during placement of the implant. If required, the tension in each individual strand may re-adjusted in the manner previously herein described.

Figure 39:
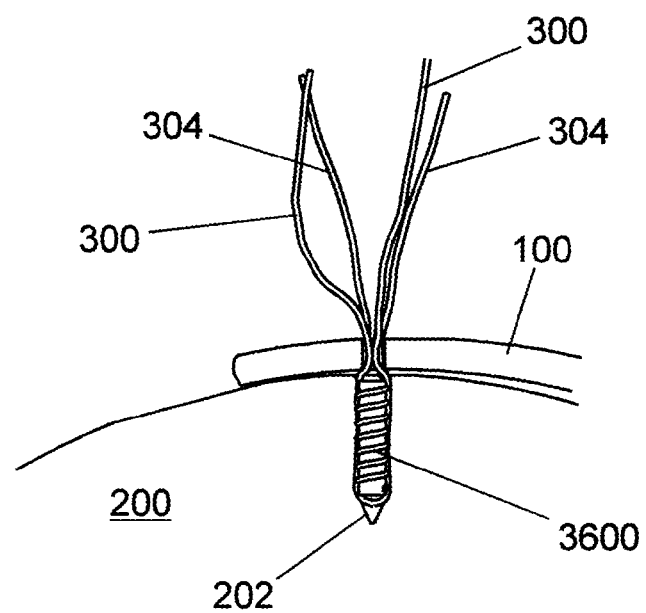
FIG. 39 depicts a medial anchor affixing two sutures to a bone for securing a graft to a prepared boney surface.
Figure 40:
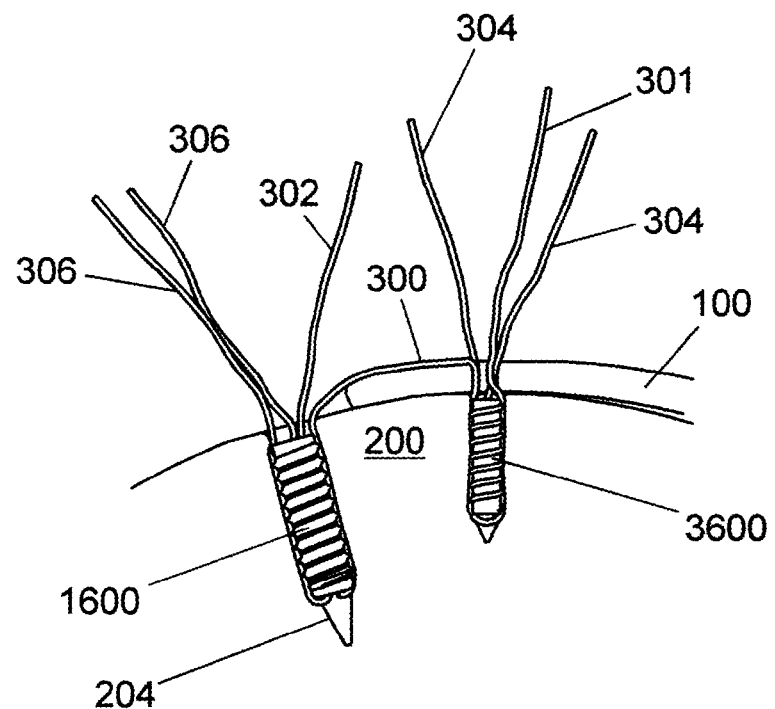
FIG. 40 depicts the completed construction of FIG. 38 with additional sutures secured by the medial and lateral anchors.

FIG. 39 depicts first suture 300 and second suture 304 secured by a medial anchor 3600 in socket 202. The limbs of suture 300 and limbs of suture 304 are not trimmed. In FIG. 40, suture 300 has been tensioned and secured by anchor 1600 in the manner previously herein described, but suture limb 302 of suture 300 has not been trimmed. Additionally, third suture 306 is secured by implant 1600. When used in a double row construct of the present invention, a leg of third suture 306 is extended from a second medial row anchor and tensioned prior to placement of implant 1600.

Hereafter are described methods of the present invention for double row constructs for securing soft tissue to an underlying boney surface. In the following illustrative examples are depicted methods for constructing a double row repair, for modifying the tension in one or more sutures within a double row construct, for repositioning an implant within a double row construct, and for adding one or more additional implants to a previously formed double row construct.

Figure 41:
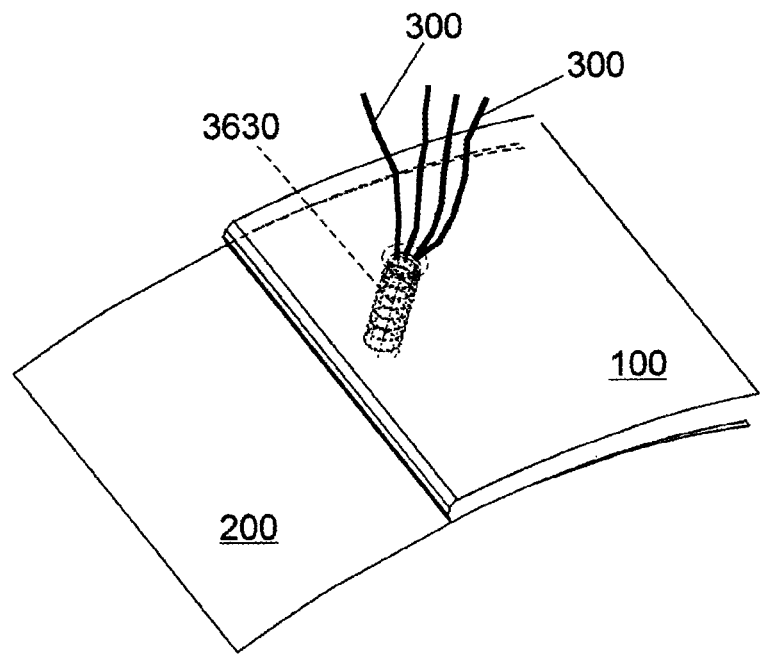
FIG. 41 is a perspective view of a placed first medial implant of a double row construct for rotator cuff reattachment according to the methods of the present invention.
Figure 42:
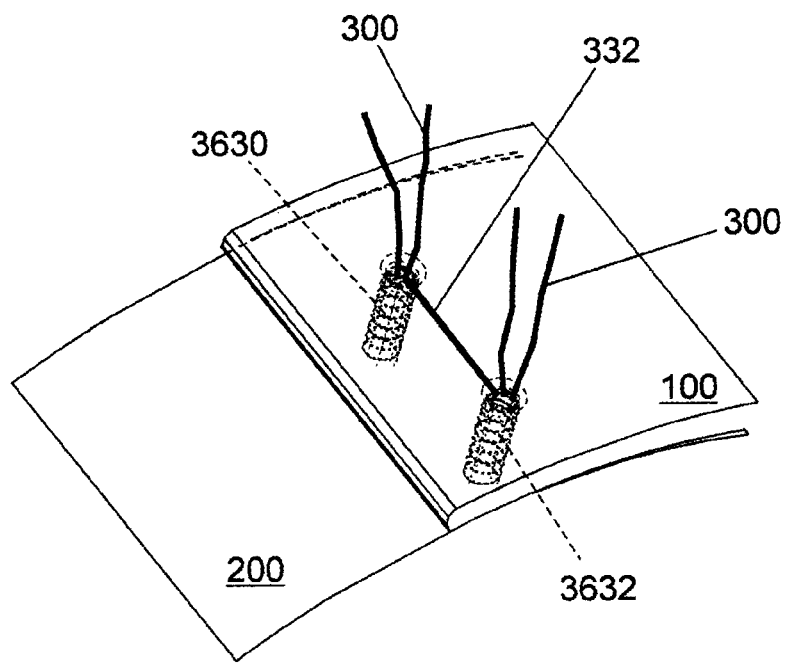
FIG. 42 is a perspective view of the first and second medial implants of a double row fixation with a tensioned suture joining the implants.
Figure 43:
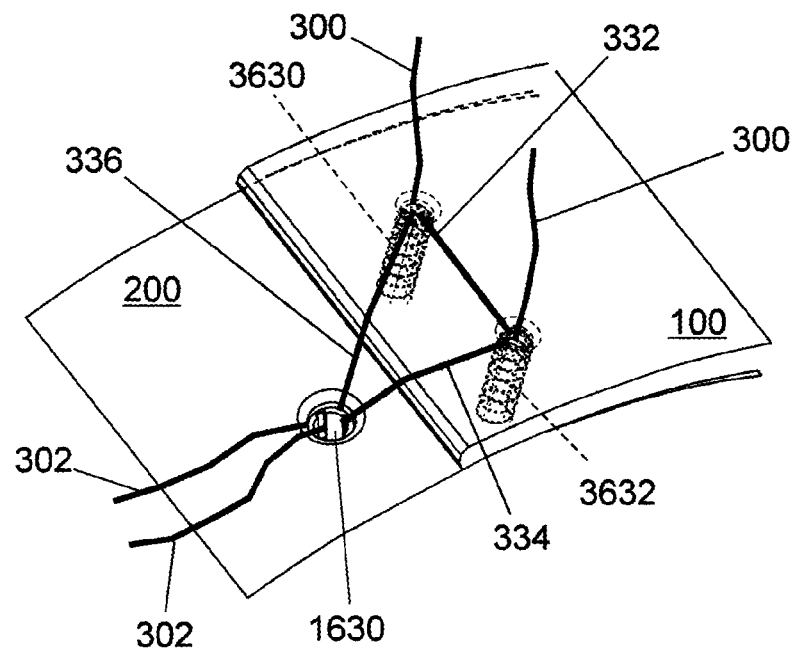
FIG. 43 is a perspective view of the medial implants of FIG. 42 and a first lateral implant placed with tensioned sutures joining the medial implants to the first lateral implant.
Figure 44:
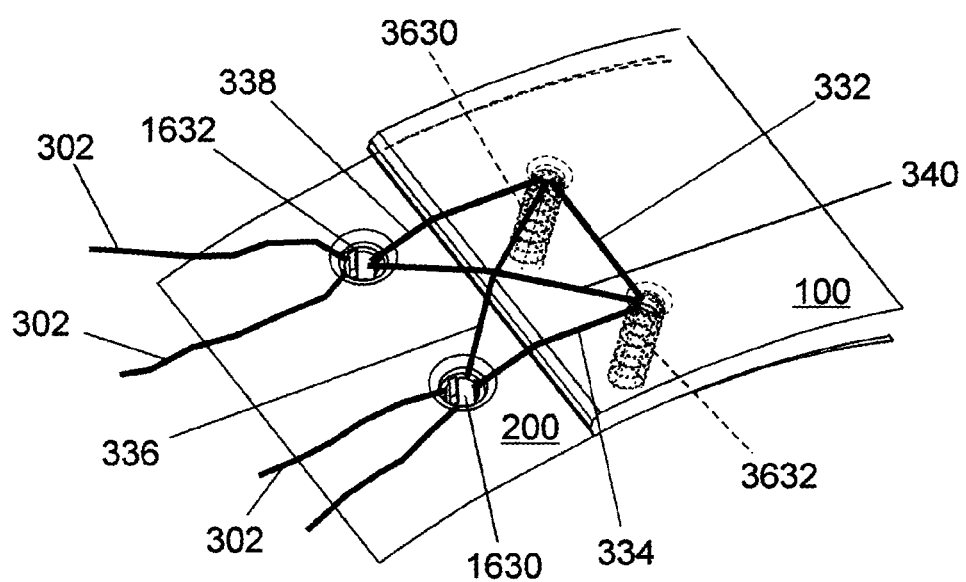
FIG. 44 is a perspective view of the elements of FIG. 43 with a second lateral implant placed and joined to the medial implants by tensioned sutures.
Figure 45:
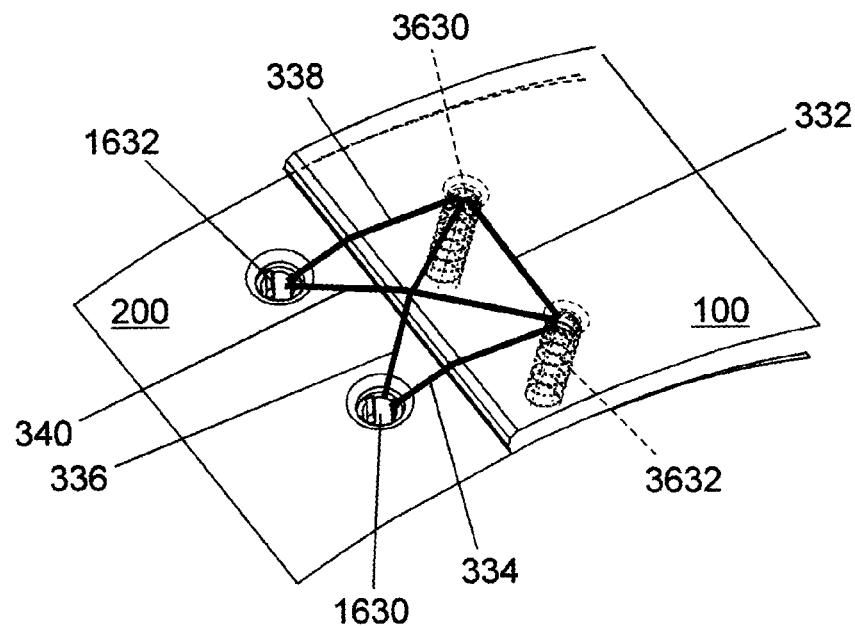
FIG. 45 is a perspective depiction of a completed double row repair using the elements of FIG. 44.

FIG. 41 depicts a first medial implant 3630 with sutures 300 placed as depicted in FIG. 39, the first step in forming a double row construct for the purpose of securing soft tissue 100 to boney surface 200. In FIG. 42, second medial implant 3632 is placed and suture 332 is tensioned during placement of implant 3632 as previously herein described. If, following placement of implant 3632 the tension in suture 332 is found to be suboptimal, implant 3632 may be backed out and the suture re-tensioned as previously herein described. Referring now to FIG. 43, subsequently, first lateral implant 1630 is placed as depicted in FIG. 40 and previously herein described. Sutures 334 and 336 are tensioned as previously herein described. If the tension in either suture is found to be suboptimal, implant 1630 may be backed out and the tension in each suture leg adjusted as previously herein described. Second medial anchor 1632 is then placed as depicted in FIG. 44 and sutures 338 and 340 tensioned, the tension being subsequently adjusted if required as previously described. With the double row construct now completed, the surgeon may examine the tension of each suture in the construct, and if any suture is determined to have suboptimal tension, to adjust the tension in that suture by backing out the appropriate implant, adjusting the suture tension and then reseating the implant. FIG. 45 depicts the double row construct with the sutures trimmed to complete the repair.

Figure 46:
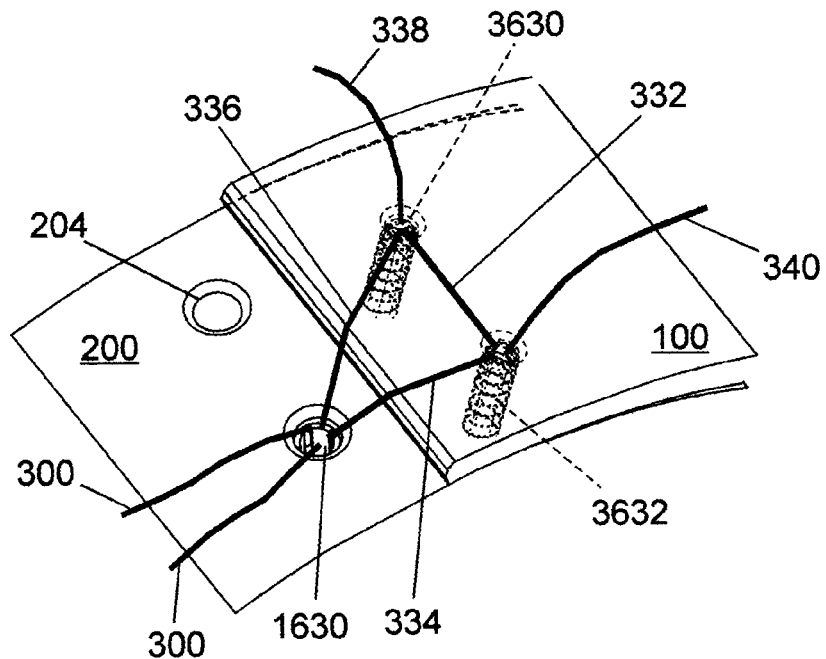
FIG. 46 is a perspective view of a double row construct of the present invention in which a lateral implant has been removed in preparation for repositioning the implant.
Figure 47:
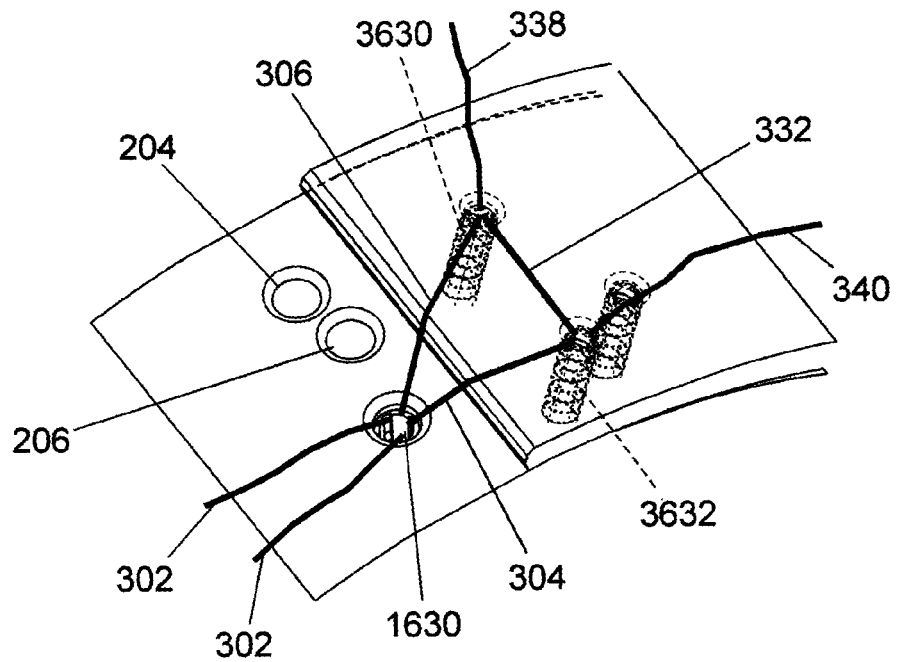
FIG. 47 is a perspective view of the elements of FIG. 46 with the addition of a socket formed in a new location.
Figure 48:
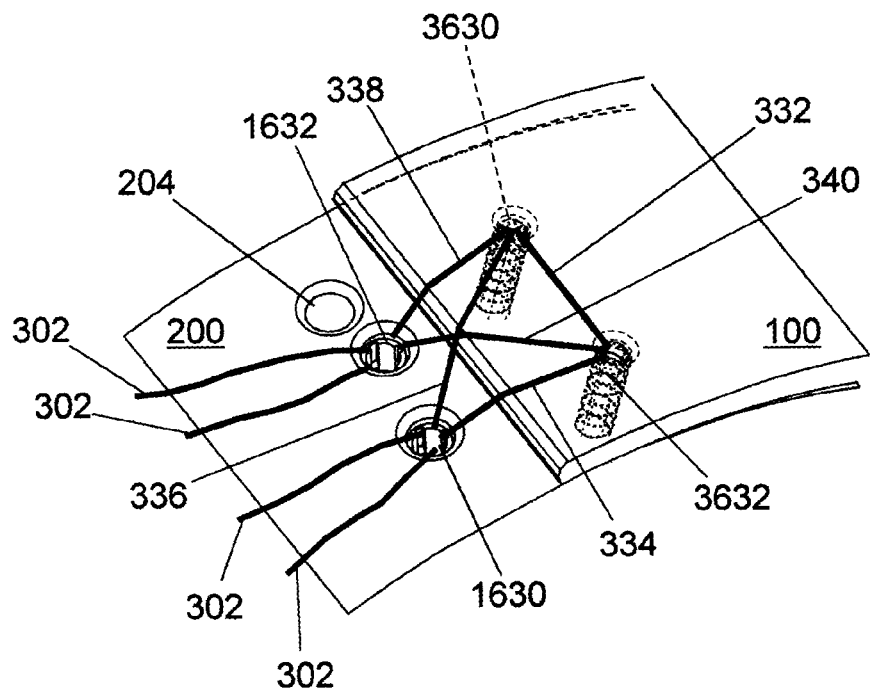
FIG. 48 is a perspective view of the elements of FIG. 47 wherein the lateral implant is placed in the socket formed in the new location and tensioned sutures connect to the medial implants.
Figure 49:
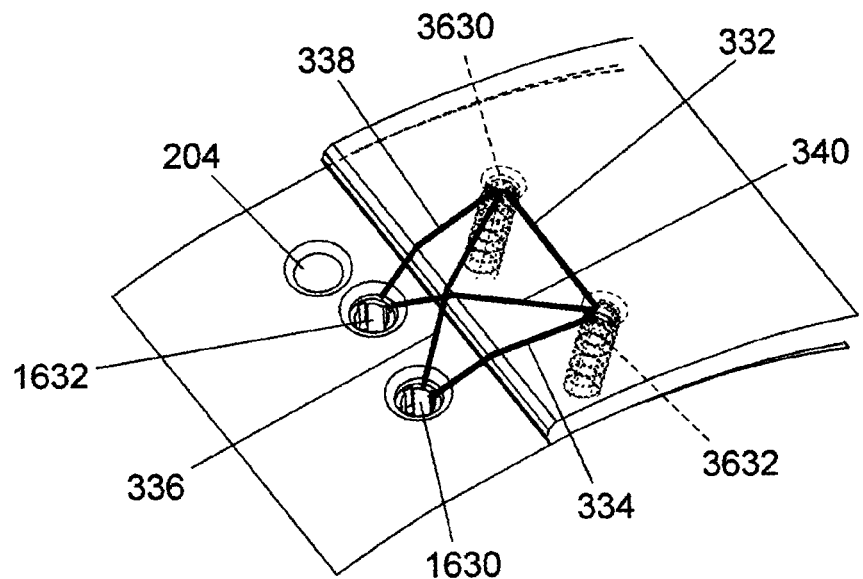
FIG. 49 is a perspective view of the modified double row construct of FIGS. 46 and 47.

Referring again to FIG. 44, if the surgeon determines that the construct is suboptimal and that the repair may be improved by repositioning of an implant, a socket may be formed in the desired implant location. Thereafter the implant to be repositioned is removed from its original socket and placed in the newly formed socket using methods previously herein described. In FIG. 46, second lateral implant 1632 has been removed from socket 204 in which it was previously placed. In FIG. 47 socket 206 has been formed in the alternate location, and in FIG. 48 implant 1632 has been placed in newly formed socket 206 and sutures 338 and 340 tensioned and affixed thereby. FIG. 49 depicts the completed repair with the suture tails trimmed.

Figure 50:
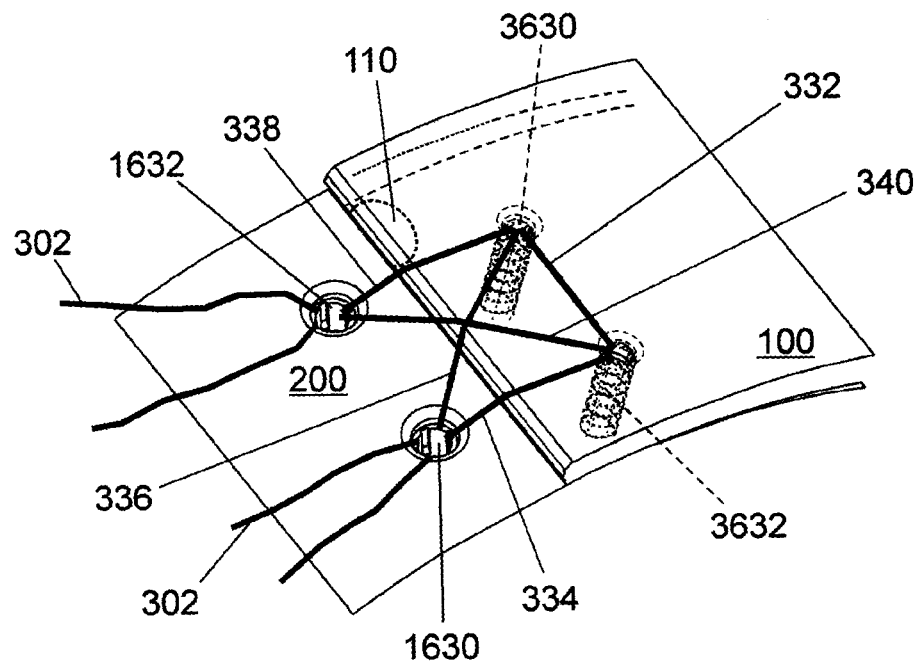
FIG. 50 depicts a double row construct of the present invention having a region adjacent to the construct in which a lateral region of the soft tissue is not in contact with the underlying bone.
Figure 51:
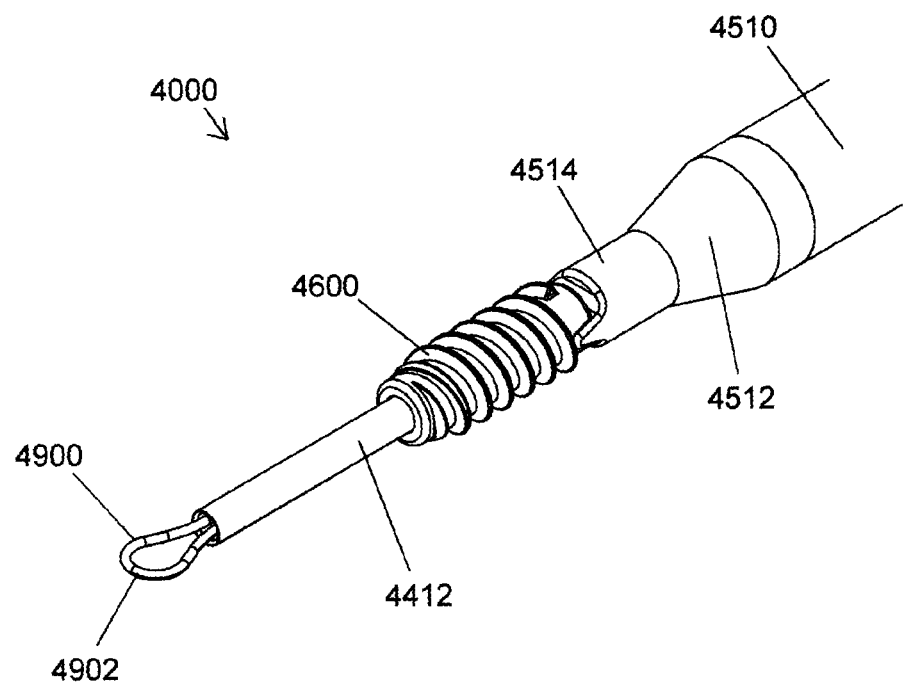
FIG. 51 is a perspective view of the distal portion of an alternate embodiment implant placement system configured for the placement of small preferably ceramic implants.
Figure 52:
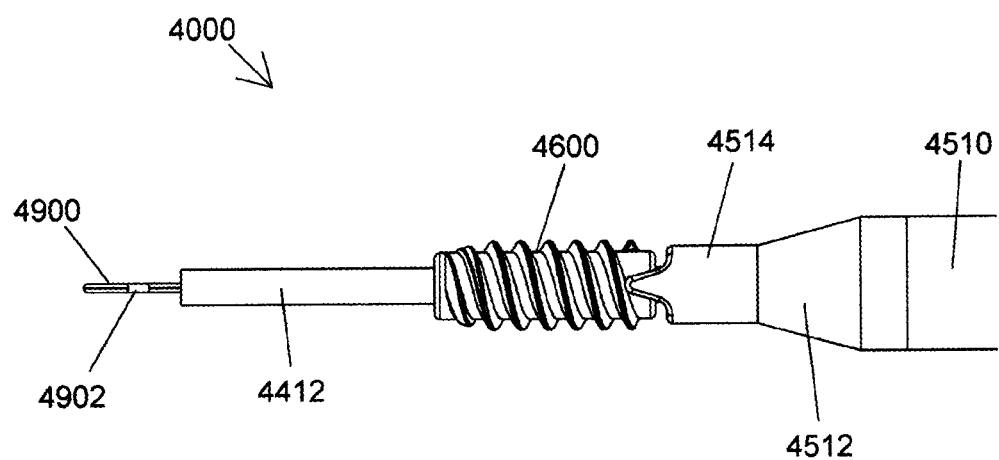
FIG. 52 is a side elevational view of the objects of FIG. 51.

FIG. 50 depicts the construct of FIG. 44 wherein a region 110 of the lateral portion of soft tissue 100 adjacent to the previously formed construct is not pressed against underlying boney surface 200. If the soft tissue within the region is not pressed to the boney surface, the repair may not result in complete reattachment of soft tissue 100 to boney surface 200. FIGS. 51 and 52 depict the distal portion of an implant placement system 4000 of the present invention configured for the placement of a small diameter implant 4600. Implant placement system 4000 is alike in all aspects of form and function to placement system 3000 except as specifically hereafter described. Implant 4600 is formed preferably of a high strength ceramic material. Ceramic implants suitable for use in the context of the present invention are described in detail in a related co-pending applications entitled "Ceramic Implant Placement Systems And Superelastic Suture Retention Loops For Use Therewith" Ser. No. 15/256,815 that was contemporaneously filed with the instant application, the entire contents of which are hereby incorporated in their entirety.

Unlike implant 3600 wherein the torque-transmitting features are located in the lumen of implant 3600, the torque-transmitting features of implant 4600 are formed in the proximal end of implant 4600. Distal portion 4514 of distal torque-transmitting element 4512 has formed on its distal end, torque-transmitting features complementary to those of implant 4600. The torque-transmitting features of implant 4600 are a laterally extending channel, with a complementary rib formed on distal portion 4514 of distal torque-transmitting element 4512. In other embodiments other complementary features are configured for torque transmission. These features are configured so that torque is effectively transmitted to implant 4600 for both insertion and removal from a socket. Due to the high strength ceramic material from which implant 4600 is formed and the unique proximal torque-transmitting features of implant 4600 which this enables, implant 4600 may have a miniaturized small-diameter construction capable of knotlessly affixing sutures in locations in which such fixation would be precluded by the larger footprint size of other knotless implants.

Figure 53:
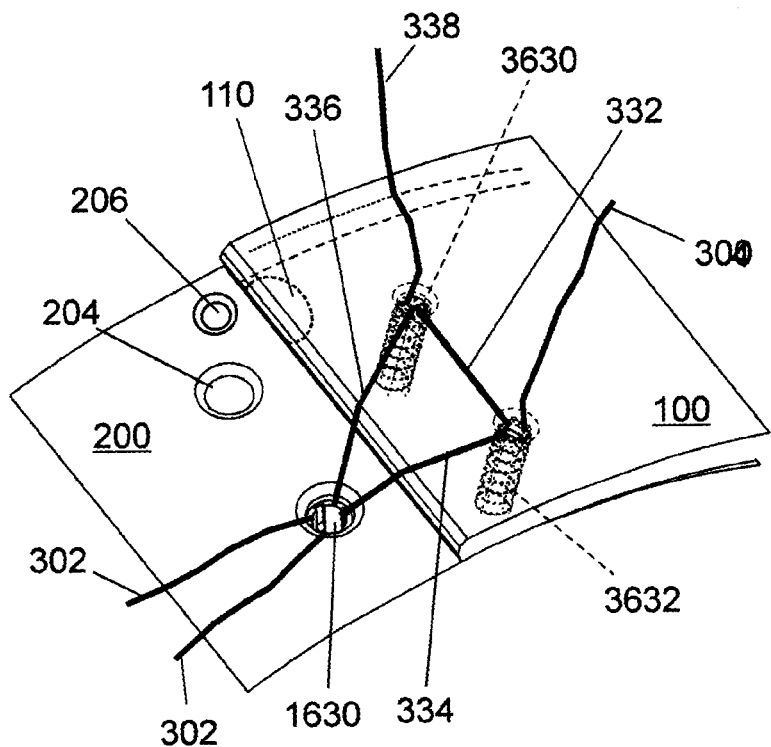
FIG. 53 depicts the objects of FIG. 50 wherein a lateral implant adjacent to the lateral region of non-contacting soft tissue is removed and a small diameter socket has been formed in proximity to the non-contacting tissue region, lateral to the edge of the soft tissue.
Figure 54:
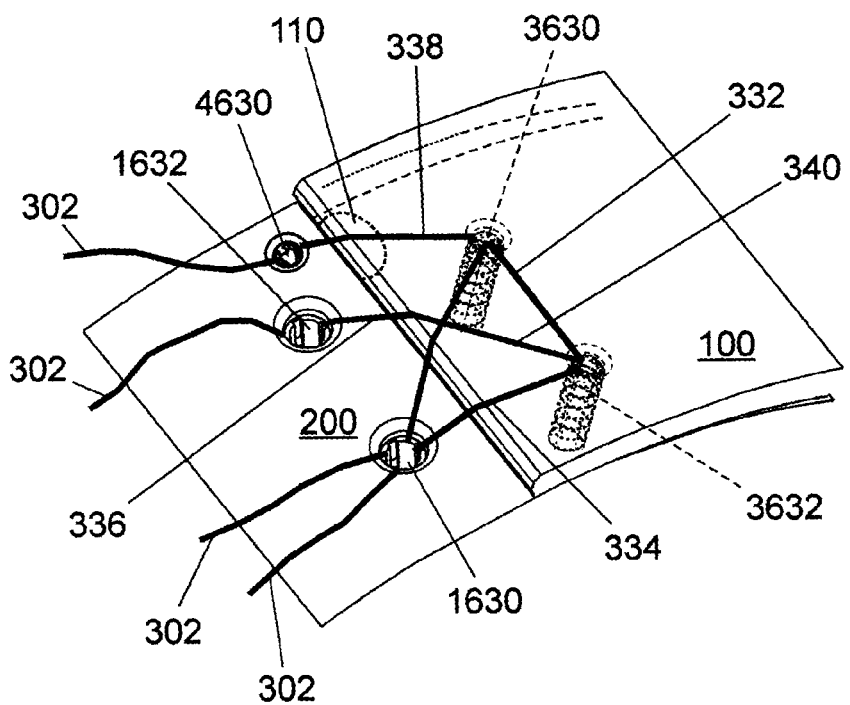
FIG. 54 depicts the objects of FIG. 54 wherein the lateral anchor which was removed is again placed in its original socket and a small anchor of the implant system of FIG. 51 is placed in the adjoining small diameter socket, with tensioned sutures spanning the soft tissue.
Figure 55:
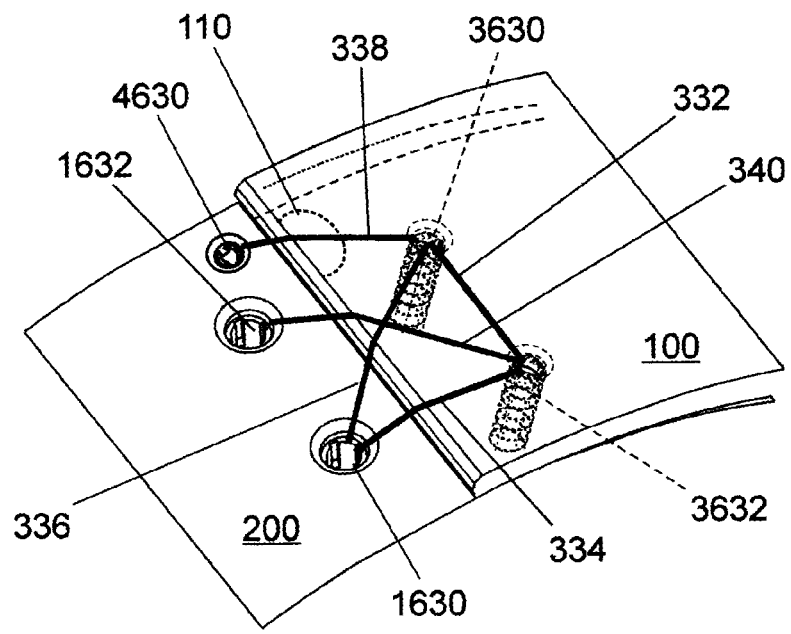
FIG. 55 depicts the completed construct of FIG. 54.

FIG. 50 depicts a double row construct of the present invention. Region 110 wherein soft tissue 100 is not pressed against underlying boney surface 200 is positioned adjacent to the construct. Tissue 100 within region 110 may be pressed to underlying boney surface 200 by supplementing the construct of FIG. 50 with implant 4630. As depicted in FIG. 53, implant 1632 is removed from socket 204 and socket 206, configured to receive implant 4630, is formed a short distance from socket 204 and laterally aligned such that suture between implant 3630 and anchor 4630 to be placed in socket 204 spans region 110 of soft tissue 100. Thereafter, as depicted in FIG. 54, suture 340 is tensioned and affixed by implant 1632 as previously described. Suture 338 is tensioned and affixed by implant 4630 in the manner previously herein described, suture 338 spanning region 110 so as to press tissue 100 therein against underlying boney surface 200. FIG. 55 depicts the completed augmented construct with the sutures trimmed.

Figure 56:
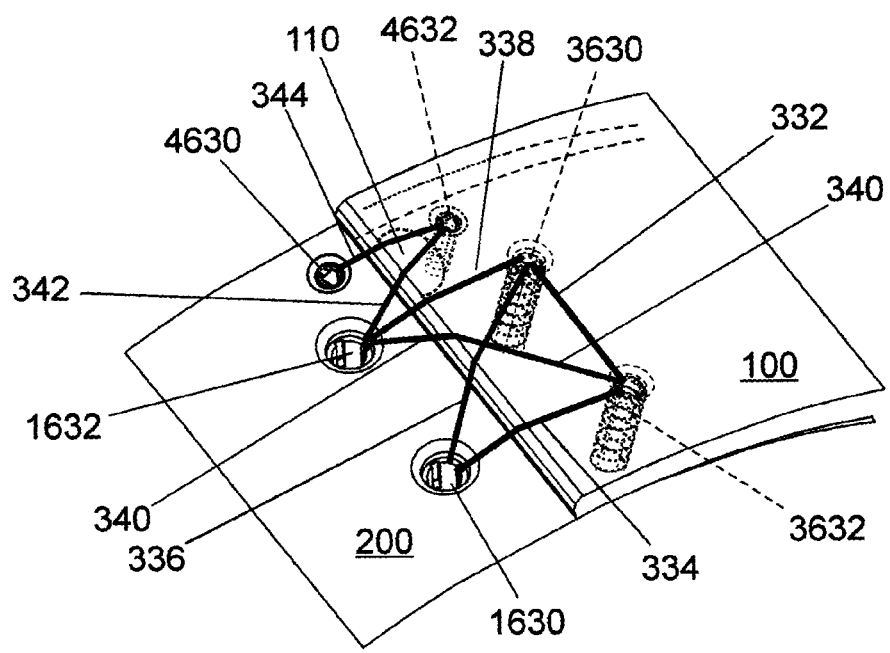
FIG. 56 depicts another repair construct in which a region of non-contacting soft tissue adjacent to the original double row construct is pressed against the underlying bone by sutures tensioned between small diameter anchors placed adjacent to the original construct.

FIG. 56 depicts an alternate construct wherein the region 110 is pressed against underlying boney surface 200 through supplementing of the original construct depicted in FIG. 50. In this construct lateral implant 4630 and a medial implant 4632 are added to the construct such that sutures 342 and 344 span region 110 so as to compress tissue 100 therein against underlying boney surface 200.

Supplementing of a completed double row construct with one or more additional implants and one or more sutures coupled to the original construct as previously described according to methods of the present invention, is enabled by the ability to remove implants of the original construct so as to allow reconfiguration of the sutures of the construct. This reconfiguration allows sutures to span tissue in the region between the original construct and the supplemental one or more implants. The ability to modify the construct is enabled by the removability of the implants. This, in turn, is enabled by the configuration of implant systems of the present invention and the threaded implants which secure suture in a socket by trapping the suture between the implant and at least a first portion of the socket wall. This is in contrast to the system of Green et al. wherein a two-piece implant system is used, sutures being fixedly secured by a separate fixation element to an anchor that is placed prior to suture tensioning. The implants of Green et al. cannot be readily removed after placement nor suture reconnected to an anchor. Similarly, the Burkhart implant system uses a first eyelet implant which is removably affixed to the end of the driver, and a second threaded implant which secures the eyelet in the socket and accomplishes suture fixation by trapping the suture between this second securing implant and portions of the socket wall. Backing out the Burkhart implants after placement and removal of the driver from the site so as to allow adjustment of the suture tension or repositioning of the implant would require that the first eyelet implant be reattached to the driver, a task which is impossible after the eyelet is removed from the driver. The adjustment of the tension in sutures of a multi-implant construct or the backing out and re-seating of implants of the construct are impossible with the Burkhart system.

Implant systems of the present invention enable the surgeon to establish suitable tension in a suture prior to implant placement, and to maintain that tension unchanged during implant placement. Accordingly, the need to adjust suture tension after implant placement is minimized. In certain instances, this removability of an implant for adjustment of the associated suture tension or repositioning of an anchor, while desirable, may not be necessary, or may be precluded by the requirement to place an irremovable push-in implant. Push-in implants of the present invention may be produced in very small sizes for applications in which a very small footprint is required. Miniature push-in implants of the present invention may be formed of a high-strength ceramic material.

Figure 57:
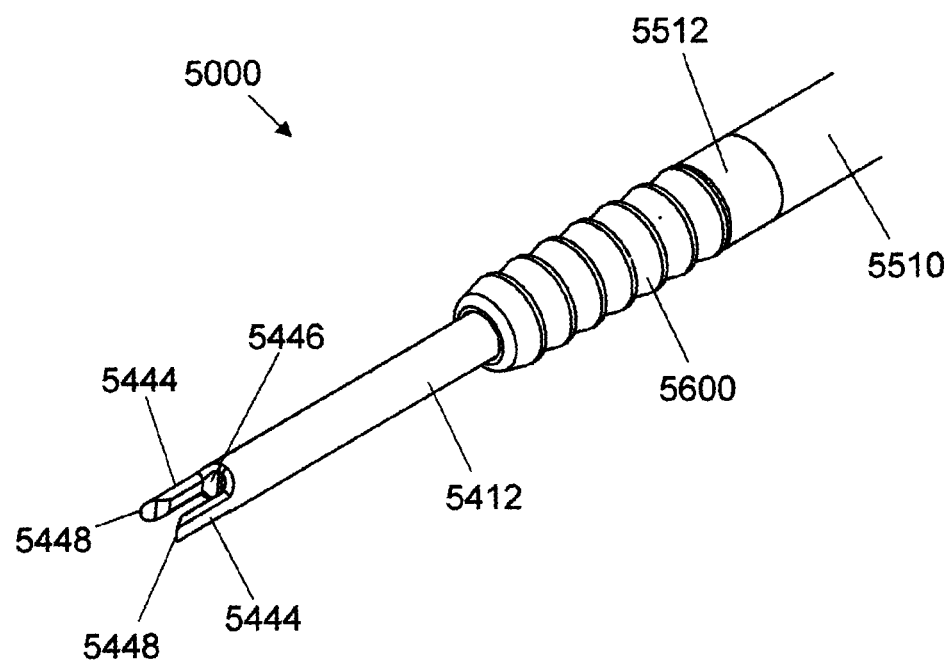
FIG. 57 depicts a perspective view the distal portion of an alternate embodiment implant placement system for use with small push-in plug-type implants.
Figure 58:
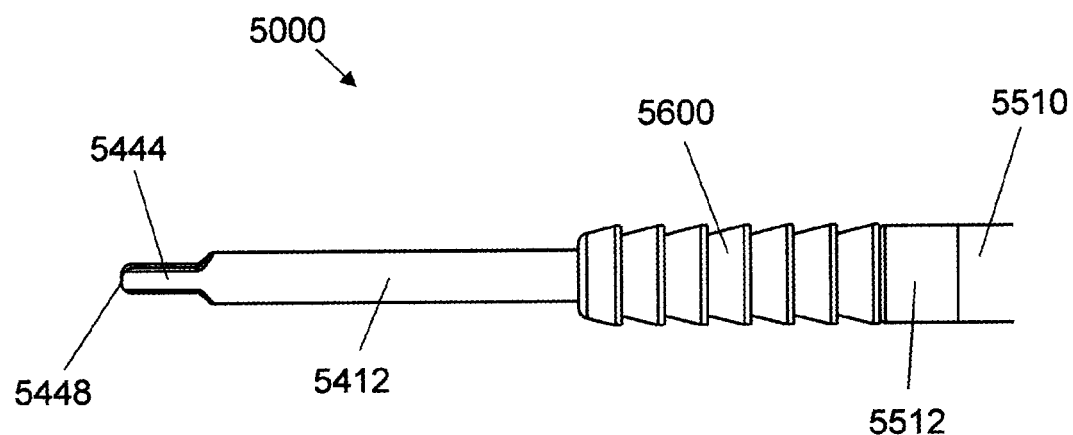
FIG. 58 is a side elevational view of the objects of FIG. 57.

Implant placement system 5000, the distal portion of which is shown in FIGS. 57 and 58, is like implant system 4000 in all aspects of form and function except as specifically subsequently described. Implant 5600 has formed on its outer surface a plurality of tapered portions that allow axial insertion into a prepared socket and that resist proximal motion of the implant after placement. Because implant 5600 is pushed axially into a socket, the torque-transmitting features of implant 4600 are eliminated and the proximal end surface of implant 5600 has a planar surface, as does the distal surface of distal element 5512 of the driver. Implant 5600 is placed in the same manner as other implants of the present invention except that, after tensioning of sutures to be secured thereby, implant 5600 is advanced to the socket and then placed therein by the surgeon striking the proximal end of the driver with a mallet so as to advance implant 5600 axially until implant 5600 is fully seated. The tension in the suture secured by implant 5600 is not changed during placement of implant 5600.

Figure 59:
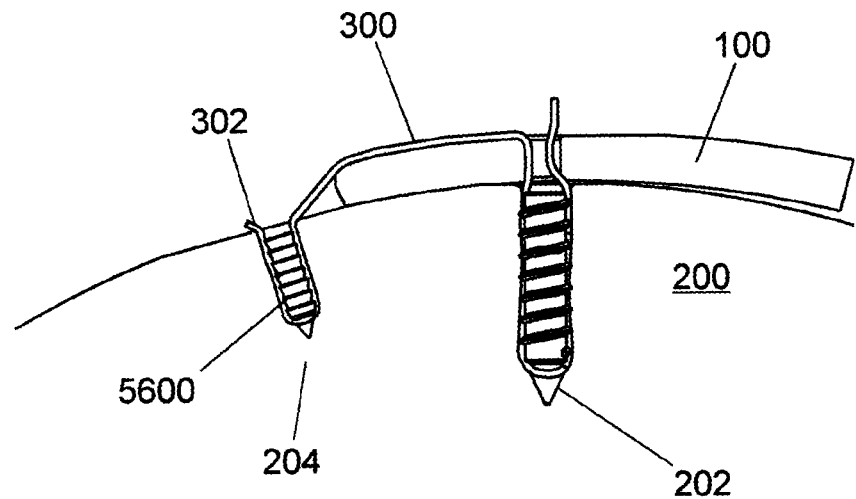
FIG. 59 depicts a two-implant repair in which the lateral anchor is a small push-in plug-type implant, the construct being formed using methods of the present invention.

FIG. 59 depicts a two-anchor construct identical to the construct of FIG. 38 in all aspects except as specifically hereafter described. For example, threaded anchor 1600 of the construct of FIG. 38 may be replaced by push-in implant 5600 (FIGS. 57 and 58). The construct of FIG. 59 is formed by the same method as the construct of FIG. 38 in all aspects except as specifically described hereafter. Following placement of medial implant 3600, suture 300 is tensioned as previously herein described and secured by implant 5600 which is pushed in rather than threaded in like lateral implant 1600 of the construct of FIG. 38. Because lateral implant 5600 is not removable after placement, adjustment of the tension in suture 300 is not possible. Because the tension is established prior to the placement of implant 5600 and is not changed during the placement of implant 5600, the tension in suture 300 in the completed construct is as intended by the surgeon.

Figure 60:
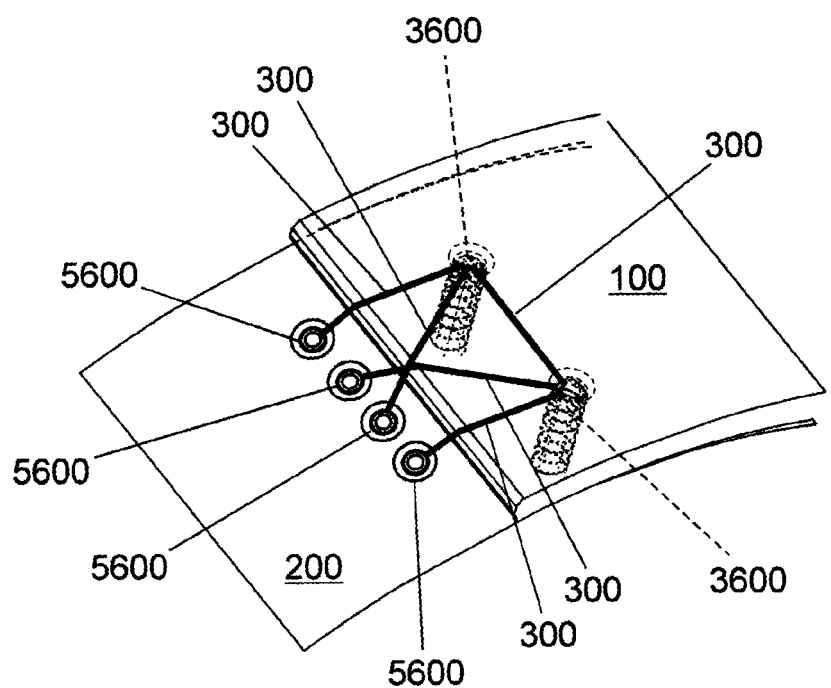
FIG. 60 depicts a double-row repair construct in which the lateral anchors are small push-in plug-type implants, the construct being formed using methods of the present invention.

FIG. 60 depicts a multi-anchor repair construct formed using methods of the present invention wherein lateral anchors 5600 are push-in implants placed using system 5000 depicted in FIGS. 57 and 58. As in the construct depicted in FIG. 59, sutures 300 are tensioned prior to placement of implants 5600. Implants 5600 are irremovable after placement using the elements of implant system 5000. The use of small diameter push-in implants 5600 may be necessitated by anatomies in which an effective multi-anchor construct requires the use of implants which have a minimal footprint.

Figure 61:
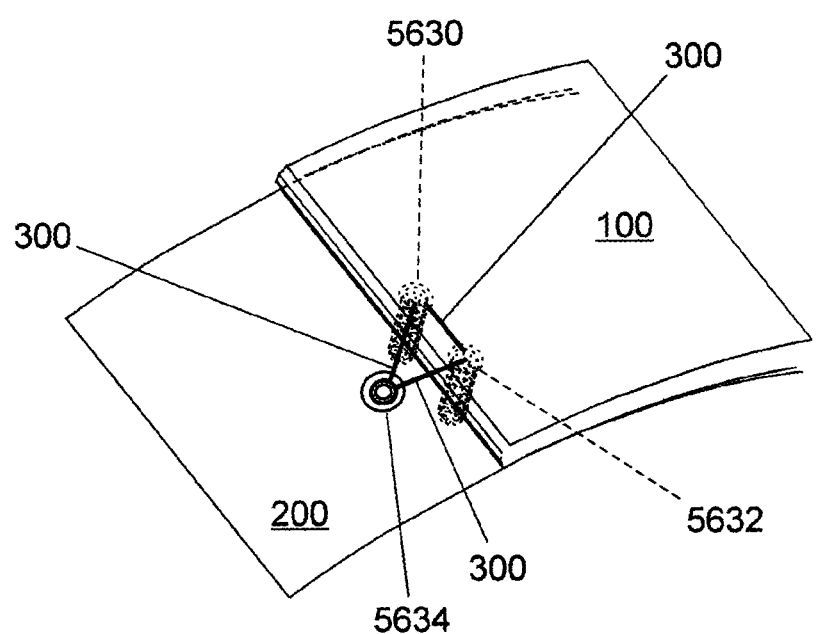
FIG. 61 depicts a repair construct with two medial implants and a single lateral implant wherein the anchors are small push-in implants, the construct being formed using methods of the present invention.

FIG. 61 depicts a multi-anchor construct in which the two medial and single lateral anchors are all small-diameter push-in implants 5600, sutures 300 being tensioned according to the principles of the present invention as previously described herein.

INDUSTRIAL APPLICABILITY

As noted previously, there is a need in the art for simplified placement systems and fixation methods for tissue graft anchors by which the surgeon may introduce one or more sutures into one or more sockets prepared in the boney tissue, apply tension to the sutures to advance a soft tissue graft to a desired location, and then advance the one or more anchors into the bone while maintaining suture tension. The present invention addresses this need by providing systems and tissue fixation methods that allows the surgeon to establish the graft position and, while maintaining that position, secure the anchor without changing the suture tension or causing a shift in the graft position and furthermore, when the anchor is threaded, without spinning of the suture. The present invention further addresses the need for double row fixation methods that allow for each tissue-spanning suture to be individually tensioned prior to, and optionally after, if the original tension is deemed unsuitable, being removably affixed to the bone by an implant. Likewise, the present invention provides for the ready relocation of any anchor found to be unsuitable as well as the placement one or more additional implants as needed to span the region with tensioned sutures. Although described in detail with respect to ligament repairs, such as repair of a torn rotator cuff, it will be readily apparent to the skilled artisan that the utility of the present invention extends to other tissues and injuries.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

The invention has been illustrated by reference to specific examples and preferred embodiments. However, it should be understood that the invention is intended not to be limited by the foregoing description, but to be defined by the appended claims and their equivalents.

What is claimed:

1. A method for affixing a soft tissue graft to a target location on a boney surface, said method comprising the steps of:
   a. positioning said soft tissue graft on said boney surface at said target location, wherein said soft tissue graft is characterized by a lateral edge and top and bottom surfaces;
   b. providing at least one elongate suture characterized by first and second free ends;
   c. securing said first free end of said suture to said boney surface by means of a first implant inserted into said boney surface underneath said soft tissue graft, at location that is medial to the lateral edge of said soft tissue graft;
   d. passing a first length of said suture that includes said second free end from said first implant over the top surface of said soft tissue graft, such that said second free end extends away from said first implant;
   e. preparing a socket in said boney surface at a predetermined location;
   f. establishing a desired tension in said first length of said suture that is sufficient to compress an area of the soft tissue graft to the boney surface that is disposed between said first implant and said predetermined location; and
   g. after said desired tension is established in accordance with step (f) and using only a second implant of one-piece construction, placing said second implant into said prepared socket so as to simultaneously fix the placement of said second free end of said suture and compress at least a portion of said first length of said suture between an outer surface of said second implant and a wall of said socket, whereby said desired tension in said first length of suture is maintained throughout step (g).

2. The method of claim 1, wherein the predetermined location of said socket is medial to the lateral edge of said soft tissue graft.

3. The method of claim 1, wherein the predetermined location of said socket is lateral to the lateral edge of said soft tissue graft.

4. The method of claim 1, wherein said soft tissue graft is further secured to said target boney surface by repeating steps b-h using third and optionally fourth implants.

5. The method of claim 4, wherein one of said second and third implants is positioned medial to the lateral edge of said soft tissue graft while the other is positioned lateral to the lateral edge of said soft tissue graft.

6. The method of claim 1, wherein said method further comprises the step of adjusting the tension in said first length of suture after placement of said second implant.

7. The method of claim 6, wherein said tension adjustment is achieved by:
   a. proximally retracting said second implant;
   b. adjusting the tension in said first length of suture; and
   c. distally advancing said second implant back into said socket until said second free end of said suture is adequately secured between the outer surface of said second implant and the wall of said socket and thus said first length of said suture is adequately tensioned so as to provide fixation to said soft tissue graft.

8. The method of claim 1, wherein said method further comprises the step of repositioning said second implant in said prepared socket.

9. The method of claim 8, wherein said repositioning step is achieved by:
   a. removing said second implant;
   b. forming a second socket in a second predetermined location;
   c. adjusting the tension in said first length of said suture; and
   d. distally advancing said second implant into said second socket until said second free end of said suture is adequately secured between the outer surface of said second implant and the wall of said second socket and thus said first length of said suture is adequately tensioned so as to provide fixation to said soft tissue graft.

10. The method of claim 1, wherein said second implant is cannulated.

11. The method of claim 10, wherein said second implant comprises an interference plug-type anchor.

12. The method of claim 10, wherein said second implant comprises a threaded anchor.

13. The method of claim 1, wherein said first implant is cannulated.

14. The method of claim 13, wherein said first implant comprises an interference plug-type anchor.

15. The method of claim 13, wherein said first implant comprises a threaded anchor.

\* \* \* \* \*